US008771991B2

(12) United States Patent
Gilbert et al.

(10) Patent No.: US 8,771,991 B2
(45) Date of Patent: Jul. 8, 2014

(54) SOAT POLYPEPTIDE REACTION MIXTURE

(75) Inventors: Michel Gilbert, Gatineau (CA); Warren Wakarchuk, Ottawa (CA); Scott Houliston, Ottawa (CA)

(73) Assignee: National Research Council of Canada, Ottawa, Ontario (CA)

( * ) Notice: Subject to any disclaimer, the term of this patent is extended or adjusted under 35 U.S.C. 154(b) by 1507 days.

(21) Appl. No.: 12/063,508

(22) PCT Filed: Aug. 11, 2006

(86) PCT No.: PCT/CA2006/001320
§ 371 (c)(1),
(2), (4) Date: Nov. 25, 2009

(87) PCT Pub. No.: WO2007/016792
PCT Pub. Date: Feb. 15, 2007

(65) Prior Publication Data
US 2010/0167349 A1    Jul. 1, 2010

Related U.S. Application Data

(60) Provisional application No. 60/707,843, filed on Aug. 11, 2005.

(51) Int. Cl.
*C12P 19/00* (2006.01)
(52) U.S. Cl.
USPC ............ 435/72; 435/7.1; 435/320.1; 435/252
(58) Field of Classification Search
None
See application file for complete search history.

(56) References Cited

FOREIGN PATENT DOCUMENTS

| WO | WO 00/46379 | 8/2000 |
|---|---|---|
| WO | WO 02/074942 | 9/2002 |

OTHER PUBLICATIONS

Seffernick et al. (J. Bacteriology, vol. 183, pp. 2405-2410, 2001).*
Wells, (Biochemistry, vol. 29, pp. 8509-8517, 1990.*
Alignment , WO200046379, Aug. 10, 2000.*
Butor et al., "High level of $O$-acetylation of sialic acids on $N$-linked oligosaccharides of rat liver membranes," *J. Biol. Chem.* 268: 10197-10206 (1993).
Claus, H. et al., "Genetics of capsule O-acetylation in serogroup C, W-135 and Y meningococci," *Mol. Microbiol.* 51: 227-239 (2004).
Downie, J. A., "The *nodL* gene from *Rhizobium leguminosarum* is homologous to the acetyl transferases encoded by *lacA* and *cysE*," *Mol. Microbiol.* 3: 1649-1651 (1989).
Gilbert et al., "The synthesis of sialylated oligosaccharides using a CMP-Neu5Ac synthetase /sialyltransferase fusion," *Nat. Biotechnol.* 16:769-772 (1998).
Gilbert et al., "Biosynthesis of ganglioside mimics in *Campylobacter jejuni* OH4384. Identification of the glycosyltransferase genes, enzymatic synthesis of model compounds, and characterization of nanomole amounts by 600-mhz $^1$h and $^{13}$c NMR analysis," *J. Biol. Chem.* 275:3896-3906 (2000).
Gilbert et al., "The genetic bases for the variation in the lipo-oligosaccharide of the mucosal pathogen, *Campylobacter jejuni*. Biosynthesis of sialylated ganglioside mimics in the core oligosaccharide," *J. Biol. Chem.* 277:327-337 (2002).
Houliston et al., "Identification of a sialate O-Acetyltransferase from *Campylobacter jejuni*: Demonstration of direct transfer to the C-9 position of terminal α-2, 8-linked sialic acid," *J. Biol. Chem.* 281:11480-11486 (2006).
Iwersen et al., "Solubilisation and properties of the sialate-4-O-acetyltransferase from guinea pig liver," *Biol. Chem.* 384:1035-1047 (2003).
Shen et al., "Characterization of the sialate-7(9)-O-acetyltransferase from the microsomes of human colonic mucosa," *Biol. Chem.* 383:307-317 (2002).
Tatusov et al., "The COG database: an updated version includes eukaryotes," *BMC Bioinformatics* 4:41 (2003).
GenBank Accession No. AF130984 (BCT date Apr. 25, 2006).
GenBank Accession No. AF167344 (BCT date Apr. 25, 2006).
GenBank Accession No. AF215659 (BCT date Apr. 25, 2006).
GenBank Accession No. AF400048 (BCT date Apr. 25, 2006).
GenBank Accession No. AF401528 (BCT date Nov. 20, 2007).
GenBank Accession No. AF401529 (BCT date Apr. 25, 2006).
GenBank Accession No. AY044868 (BCT date Jan. 3, 2002).
GenBank Accession No. AY297047 (BCT date Jul. 28, 2003).
GenBank Accession No. AY779018 (BCT date Apr. 13, 2005).
GenBank Accession No. Y13969 (BCT date Apr. 18, 2005).

* cited by examiner

*Primary Examiner* — Hope Robinson
(74) *Attorney, Agent, or Firm* — Pasternak Patent Law; Dahna S. Pasternak

(57) ABSTRACT

The invention relates to sialate-O-acetyltransferase (SOAT) polypeptides, nucleic acids that encode the polypeptides, and methods of using the polypeptides.

10 Claims, 9 Drawing Sheets

```
                    10        20        30        40        50        60        70        80
                    |         |         |         |         |         |         |         |
43449       ................................................I..K.-Q...AA.L....C.........G.....
43456       ................................................I..K..Q...AA.L....C.........G.....
43438       ................................................I..E..R...AG.-....C.........G.....
43432       ................................................I..E..Q...VA.L....Y.........G.....
43446       ................................................F..E:.Q...VA.L....C.........G.....
OH4382/4384 ................................................F..E..Q...VA.L....C.........D.....
Prim.cons.  ********************************************** ** .**;.***.*  *****.***********.*****
            MEKITLKCNKNILNLLKQINIYTKTYIENPRRFSRLKTKDFITIPLENNQLESAAGLGIEEYCAFKFSNILHEMGSFSFS 90        100       110       120       130       140       150       160
                    |         |         |         |         |         |         |         |
43449       .......A..G....A.........I.................D......................................
43456       .......A..E....A.........I.................D......................................
43438       .......A..G....A.........I.................D......................................
43432       .......A..G....A.........M.................N......................................
43446       .......T..G....S.........M.................D......................................
OH4382/4384 .......T..G....S.........M.................D......................................
Prim.cons.  *******.**;** ********** ******************;***********.********************************
            GSFLPHYAKVGRYCSIADGVSMFNFQHPMDRISTASFTYETNHSFINDACQNHINKTFPIVNHNPSSSITHLLIQDDVWI
```

Fig. 2A

```
                    170       180       190       200       210       220       230       240
                    |         |         |         |         |         |         |         |
43449      ........ .......... .......... .......... ....DE.... .......R.. .......... ........
43456      ........ .......... .......... .......... ....DE.... .......R.. .......... ........
43438      ........ .......... .......... .......... ....NE.... .......R.. .......... ........
43432      ........ .......... .......... .......... ....NK.... .......K.. .......... ........
43446      ........ .......... .......... .......... ....DE.... .......K.. .......... ........
OH4382/4384 ******** ********** ********** ********** ********** ********** ********** ********
Prim.cons. GKDVLLKQGITLGTGCVIGQRAVVTKDVPFYAIVAGIPAKIIKYRFDEKTIERLLKIQWKYHFADFYDIDLNLKINQYL 250       260       270
                    |         |         |
43449      .......... .......... .......   277
43456      .......... .......... .......   277
43438      .......... .......... ......    276
43432      .......... .......... .......   277
43446      .......... .......... .......   277
OH4382/4384 ********** ********** *******
Prim.cons. DLLEEKIIKKSISYYNPNKLYERDILELKSKKIFNLF
```

*Fig. 2B* gnl|CDD|9985 COG0110, WbbJ, Acetyltransferase (isoleucine patch superfamily) [General function prediction only].
CD-Length = 190 residues, only 69.5% aligned
Score = 90.0 bits (222), Expect = 3e-19

```
Query:  78   FSGSFLPHYAKVGRYCSIADGVSMF---NFQHPIDRISTASFTYETNHSFINDACQNHIN  134
Sbjct:  59   VRIDLGEKNLTIGDLCFIGVNVVILVGEGITIGDNVVGPNVTIYTNSHPGDFVTANI--   116

Query:  135  KTFPIVNHNPSSSITHLIIQDDVWIGKDVLLKQGITLGTGCVIGQRAVVTKDVPPYAIVA  194
Sbjct:  117  --GALVGAGPV-----TIGEDVWIGAGAVILPGVTIGEGAVIGAGSVVTKDVPPYGIVA  168

Query:  195  GIPAKIKYRFNEKTIERLLKI  216
Sbjct:  169  GNPARVIRKRDVVAKIGVLLAP  190
```

FIG. 4

```
              10         20         30         40         50         60         70         80
              |          |          |          |          |          |          |          |
NeuO       MLRLKTQDSRLKTQDSRLKTQDSRLKTQDSRLKTQDSRLKTQDSRLKTQDSRLKTQDSRLKTQDSFSVDDNGS
OatY       ----------------------------------------------------MGTHMYSEQGINNTINISTTSLTNATQLTVIGNN-
Orf11      ----------------------------------------MEKITLKCNRNIINLLKQYNIYTKTYIENPRRESRLKTKD
                                                            :   :..    :  :::    .

Prim.cons. MLRLKTQDSRLKTQDSRLKTQDSRLKTQDSRLK22222LKT3333L3333333333T3L3N333ESV33N32

90        100        110        120        130        140        150        160
              |          |          |          |          |          |          |          |
NeuO       -GNVFVCGDLVNSKENKVQFNGNNNKLIIEDDVECRWLTVIFRGDNNYVRIHKNSKIKGDIVATKGSKVIIGRRTTIGAG
OatY       --NSVYIGNNCKIVSSNIRLKGNNITLFIADDVENMGLVCSLHSD-------------------CS-LQIQAKTTMGNG
Orf11      FITIPLENNRLESAGGGIEEYCAFKFSNILHEMGSFSFSGSFLPHY-----------------AKVGRYCSIADGVSMFNE
                  .  :   *.  :  :        *      .:.:      *          .::

Prim.cons. F2N3333GN333S3333I333GNN33L3I3DDVE333L33SF33D2NYVRIHKNSKIKGDIVA22GS233I333TTMGNG 170        180        190        2000       210        220        230        240
              |          |          |          |          |          |          |          |
NeuO       FEVVTDKCNVTIGHDCMIARDVILRASDGHPIFDIHSKKRINWAKDIIISSYVWVGRNVSIMKGVSVSGGSVIGYGSIVT
OatY       EITIAEKGKISIGKDCMLAHGYEIRNTDMHPIYSLENGERINHGKDVIIGNHVWLGRNVTILKGVCIPNNVVVGSHTVLY
Orf11      QHPIDRISTASFTYETNHSFINDACQNHINKTEPIVNHNPSSSITHLIIQDDVWIGKDVLLKQGITLGTGCVIGQRAVVT
             .:.  :.    .:.       .:**  . **::*:*. ..:** . :*:* ..*:* ::.

Prim.cons. 333I33K333S333SIG3DCM3A33333R33D3HPIF3I3N33RIN33KD3II333VW3GRNV3I3KGV33G3VIG333VVT
```

FIG. 5A

```
              250         260         270         280         290         300         310         320
               |           |           |           |           |           |           |           |
NeuO      KDVP-SMCAAAGNPAKIIKR------------------NIIWARTDKAELISDDK--RCSSYHAKLTQ----------------------
OatY      KSFKEPNCVIAGSPAKIVKE------------------NIVWGRKMYHSTMYDDP--TLNEFYK-----------------------
Orf11     KDVP-PYAIVAGIPAKIIKYRFNEKTIERLLKIQWMRYHFADFYDIDLNLKINQYLDLLEEKIIKKSISYNPNKLYFRD
           *.  .  **  ****:*    :*:**  .  .   *             *
Prim.cons. KDVPEP3C33AG3PAKIIK3RFNEKTIERLLNI3W3R333A3333DD3NL33N3Y332L22KIIKKSISYNPNKLYFRD 330
               |
NeuO      ------------
OatY      ------------
Orf11     ILELKSKKIFNLF Prim.cons. ILELKSKKIFNLF
```

FIG. 5B

SEQUENCE LISTING

<160> NUMBER OF SEQ ID NOS: 33

<210> SEQ ID NO 1
<211> LENGTH: 834
<212> TYPE: DNA
<213> ORGANISM: Campylobacter jejuni
<220> FEATURE:
<221> NAME/KEY: misc_feature
<223> OTHER INFORMATION: strain OH4384, Orf 11 sialate-O-
acetyltransferase (SOAT)

<400> SEQUENCE: 1

| | | |
|---|---|---|
| atggaaaaaa taaccttaaa atgcaataaa aatatattaa atttattaaa gcaatataat | 60 |
| atttatacaa aaacttatat agaaaatcct agaagatttt caagactaaa aaccaaagat | 120 |
| tttataacct ttccattgga aaacaatcaa ctagagagtg tagcggggct ggggatagaa | 180 |
| gaatattgtg cttttaaatt tagcaatatc ttacatgaaa tggattcatt ttcttttagc | 240 |
| ggatcttttc tacctcatta tacaaaagtt ggaaggtatt gttcaatttc tgatggggtt | 300 |
| tctatgttta actttcaaca tcctatggat agaatcagca ctgcaagttt tacctatgaa | 360 |
| acaaatcata gttttattaa cgatgcttgc caaaatcaca tcaacaaaac atttcctata | 420 |
| gttaaccata atccaagctc atcaataacg catttaatta tacaagatga tgtttggata | 480 |
| ggaaaagatg ttttgcttaa acagggtatc acacttggga ctggatgtgt cataggacaa | 540 |
| agagctgtag ttactaaaga tgtaccacct tatgctatag ttgcaggaat tccagccaaa | 600 |
| attatcaaat atagatttga tgaaaaaaca atagaaagat tattaaaaat tcaatggtgg | 660 |
| aaatatcatt ttgctgattt ttatgatatt gatcttaatt taaaaataaa ccaatatctt | 720 |
| gacctactag aagaaaaaat cataaaaaaa tcaatttcct actataatcc aaataaactt | 780 |
| tattttagag atattttaga actaaaatca aaaaaaattt ttaatctatt ttaa | 834 |

<210> SEQ ID NO 2
<211> LENGTH: 277
<212> TYPE: PRT
<213> ORGANISM: Campylobacter jejuni
<220> FEATURE:
<221> NAME/KEY: MISC_FEATURE
<223> OTHER INFORMATION: strain OH4384, Orf 11 sialate-O-
acetyltransferase (SOAT)

<400> SEQUENCE: 2

Met Glu Lys Ile Thr Leu Lys Cys Asn Lys Asn Ile Leu Asn Leu Leu
1               5                   10                  15

Lys Gln Tyr Asn Ile Tyr Thr Lys Thr Tyr Ile Glu Asn Pro Arg Arg
            20                  25                  30

Phe Ser Arg Leu Lys Thr Lys Asp Phe Ile Thr Phe Pro Leu Glu Asn
        35                  40                  45

Asn Gln Leu Glu Ser Val Ala Gly Leu Gly Ile Glu Glu Tyr Cys Ala
    50                  55                  60

Phe Lys Phe Ser Asn Ile Leu His Glu Met Asp Ser Phe Ser Phe Ser
65                  70                  75                  80

Gly Ser Phe Leu Pro His Tyr Thr Lys Val Gly Arg Tyr Cys Ser Ile
                85                  90                  95

Ser Asp Gly Val Ser Met Phe Asn Phe Gln His Pro Met Asp Arg Ile
            100                 105                 110

Ser Thr Ala Ser Phe Thr Tyr Glu Thr Asn His Ser Phe Ile Asn Asp
        115                 120                 125

Ala Cys Gln Asn His Ile Asn Lys Thr Phe Pro Ile Val Asn His Asn
    130                 135                 140

Pro Ser Ser Ser Ile Thr His Leu Ile Ile Gln Asp Asp Val Trp Ile
145                 150                 155                 160

Gly Lys Asp Val Leu Leu Lys Gln Gly Ile Thr Leu Gly Thr Gly Cys
                165                 170                 175

Val Ile Gly Gln Arg Ala Val Val Thr Lys Asp Val Pro Pro Tyr Ala
            180                 185                 190

Ile Val Ala Gly Ile Pro Ala Lys Ile Ile Lys Tyr Arg Phe Asp Glu
            195                 200                 205

Lys Thr Ile Glu Arg Leu Leu Lys Ile Gln Trp Trp Lys Tyr His Phe
210                 215                 220

Ala Asp Phe Tyr Asp Ile Asp Leu Asn Leu Lys Ile Asn Gln Tyr Leu
225                 230                 235                 240

Asp Leu Leu Glu Glu Lys Ile Lys Lys Ser Ile Ser Tyr Asn
            245                 250                 255

Pro Asn Lys Leu Tyr Phe Arg Asp Ile Leu Glu Leu Lys Ser Lys Lys
            260                 265                 270

Ile Phe Asn Leu Phe
            275

<210> SEQ ID NO 3
<211> LENGTH: 834
<212> TYPE: DNA
<213> ORGANISM: Campylobacter jejuni
<220> FEATURE:
<221> NAME/KEY: misc_feature
<223> OTHER INFORMATION: strain OH4382, Orf 11 sialate-O-
      acetyltransferase (SOAT)

<400> SEQUENCE: 3
atggaaaaaa taaccttaaa atgcaataaa aatatattaa atttattaaa gcaatataat     60
atttatacaa aaacttatat agaaaatcct agaagatttt caagactaaa aaccaaagat    120
tttataacct ttccattgga aaacaatcaa ctagagagtg tagcggggct ggggatagaa    180
gaatattgtg cttttaaatt tagcaatatc ttacatgaaa tggattcatt ttcttttagc    240
ggatcttttc tacctcatta tacaaaagtt ggaaggtatt gttcaatttc tgatggggtt    300
tctatgttta actttcaaca tcctatggat agaatcagca ctgcaagttt tacctatgaa    360
acaaatcata gttttattaa cgatgcttgc caaaatcaca tcaacaaaac atttcctata    420
gttaaccata atccaagctc atcaataacg catttaatta tacaagatga tgtttggata    480
ggaaaagatg ttttgcttaa acagggtatc acacttggga ctggatgtgt cataggacaa    540
agagctgtag ttactaaaga tgtaccacct tatgctatag ttgcaggaat tccagccaaa    600
attatcaaat atagatttga tgaaaaaaca atagaaagat tattaaaaat tcaatggtgg    660
aaatatcatt ttgctgattt ttatgatatt gatcttaatt taaaaataaa ccaatatctt    720
gacctactag aagaaaaaat cataaaaaaa tcaatttcct actataatcc aaataaactt    780
tattttagag atattttaga actaaaatca aaaaaatttt ttaatctatt ttaa          834

<210> SEQ ID NO 4
<211> LENGTH: 277
<212> TYPE: PRT
<213> ORGANISM: Campylobacter jejuni
<220> FEATURE:
<221> NAME/KEY: MISC_FEATURE
<223> OTHER INFORMATION: strain OH4382, Orf 11 sialate-O-
      acetyltransferase (SOAT)

<400> SEQUENCE: 4

Met Glu Lys Ile Thr Leu Lys Cys Asn Lys Asn Ile Leu Asn Leu Leu
1               5                   10                  15

Lys Gln Tyr Asn Ile Tyr Thr Lys Thr Tyr Ile Glu Asn Pro Arg Arg
            20                  25                  30

```
Phe Ser Arg Leu Lys Thr Lys Asp Phe Ile Thr Phe Pro Leu Glu Asn
            35                  40                  45

Asn Gln Leu Glu Ser Val Ala Gly Leu Gly Ile Glu Glu Tyr Cys Ala
 50                  55                  60

Phe Lys Phe Ser Asn Ile Leu His Glu Met Asp Ser Phe Ser Phe Ser
 65                  70                  75                  80

Gly Ser Phe Leu Pro His Tyr Thr Lys Val Gly Arg Tyr Cys Ser Ile
                 85                  90                  95

Ser Asp Gly Val Ser Met Phe Asn Phe Gln His Pro Met Asp Arg Ile
            100                 105                 110

Ser Thr Ala Ser Phe Thr Tyr Glu Thr Asn His Ser Phe Ile Asn Asp
            115                 120                 125

Ala Cys Gln Asn His Ile Asn Lys Thr Phe Pro Ile Val Asn His Asn
130                 135                 140

Pro Ser Ser Ser Ile Thr His Leu Ile Ile Gln Asp Asp Val Trp Ile
145                 150                 155                 160

Gly Lys Asp Val Leu Leu Lys Gln Gly Ile Thr Leu Gly Thr Gly Cys
                165                 170                 175

Val Ile Gly Gln Arg Ala Val Val Thr Lys Asp Val Pro Pro Tyr Ala
            180                 185                 190

Ile Val Ala Gly Ile Pro Ala Lys Ile Ile Lys Tyr Arg Phe Asp Glu
            195                 200                 205

Lys Thr Ile Glu Arg Leu Leu Lys Ile Gln Trp Trp Lys Tyr His Phe
            210                 215                 220

Ala Asp Phe Tyr Asp Ile Asp Leu Asn Leu Lys Ile Asn Gln Tyr Leu
225                 230                 235                 240

Asp Leu Leu Glu Glu Lys Ile Ile Lys Lys Ser Ile Ser Tyr Tyr Asn
                245                 250                 255

Pro Asn Lys Leu Tyr Phe Arg Asp Ile Leu Glu Leu Lys Ser Lys Lys
                260                 265                 270

Ile Phe Asn Leu Phe
            275

<210> SEQ ID NO 5
<211> LENGTH: 834
<212> TYPE: DNA
<213> ORGANISM: Campylobacter jejuni
<220> FEATURE:
<221> NAME/KEY: misc_feature
<223> OTHER INFORMATION: strain HB93-13, Orf 11 sialate-O-
      acetyltransferase (SOAT)

<400> SEQUENCE: 5
atggaaaaaa taaccttaaa atgcaataaa aatatattaa atttattaaa gcaatataat      60
atttatacaa aaacttatat agaaaatcct agaagatttt caagactaaa aaccaaagat     120
tttataacct ttccattgga aaacaatcaa ctagagagtg tagcggggct ggggatagaa     180
gaatattgtg cttttaaatt tagcaatatc ttacatgaaa tgggttcatt ttcttttagc     240
ggatcttttc tacctcatta taaaaagtt ggaaggtatt gttcaatttc tgatggggtt     300
tctatgttta actttcaaca tcctatggat agaatcagca ctgcaagttt tacctatgaa     360
acaaatcata gttttattaa cgatgcttgc caaaatcaca tcaacaaaac atttcctata     420
gttaaccata atccaagctc atcaataacg catttaatta tacaagatga tgtttggata     480
ggaaaagatg tttttgcttaa acagggtatc acacttggga ctggatgtgt cataggacaa     540
```

```
agagctgtag ttactaaaga tgtaccacct tatgctatag ttgcaggaat tccagccaaa    600
attatcaaat atagatttga tgaaaaaaca atagaaagat tattaaaaat tcaatggtgg    660
aaatatcatt ttgctgattt ttatgatatt gatcttaatt taaaaataaa ccaatatctt    720
gacctactag aagaaaaaat cataaaaaaa tcaatttcct actataatcc aaataaactt    780
tattttagag atattttaga actaaaatca aaaaaaattt ttaatctatt ttaa          834
```

<210> SEQ ID NO 6
<211> LENGTH: 277
<212> TYPE: PRT
<213> ORGANISM: Campylobacter jejuni
<220> FEATURE:
<221> NAME/KEY: MISC_FEATURE
<223> OTHER INFORMATION: strain HB93-13, Orf 11 sialate-O-
      acetyltransferase (SOAT)

<400> SEQUENCE: 6

```
Met Glu Lys Ile Thr Leu Lys Cys Asn Lys Asn Ile Leu Asn Leu Leu
1               5                   10                  15

Lys Gln Tyr Asn Ile Tyr Thr Lys Thr Tyr Ile Glu Asn Pro Arg Arg
            20                  25                  30

Phe Ser Arg Leu Lys Thr Lys Asp Phe Ile Thr Phe Pro Leu Glu Asn
        35                  40                  45

Asn Gln Leu Glu Ser Val Ala Gly Leu Gly Ile Glu Glu Tyr Cys Ala
    50                  55                  60

Phe Lys Phe Ser Asn Ile Leu His Glu Met Gly Ser Phe Ser Phe Ser
65                  70                  75                  80

Gly Ser Phe Leu Pro His Tyr Thr Lys Val Gly Arg Tyr Cys Ser Ile
                85                  90                  95

Ser Asp Gly Val Ser Met Phe Asn Phe Gln His Pro Met Asp Arg Ile
            100                 105                 110

Ser Thr Ala Ser Phe Thr Tyr Glu Thr Asn His Ser Phe Ile Asn Asp
        115                 120                 125

Ala Cys Gln Asn His Ile Asn Lys Thr Phe Pro Ile Val Asn His Asn
    130                 135                 140

Pro Ser Ser Ser Ile Thr His Leu Ile Ile Gln Asp Asp Val Trp Ile
145                 150                 155                 160

Gly Lys Asp Val Leu Leu Lys Gln Gly Ile Thr Leu Gly Thr Gly Cys
                165                 170                 175

Val Ile Gly Gln Arg Ala Val Val Thr Lys Asp Val Pro Pro Tyr Ala
            180                 185                 190

Ile Val Ala Gly Ile Pro Ala Lys Ile Ile Lys Tyr Arg Phe Asp Glu
        195                 200                 205

Lys Thr Ile Glu Arg Leu Leu Lys Ile Gln Trp Trp Lys Tyr His Phe
    210                 215                 220

Ala Asp Phe Tyr Asp Ile Asp Leu Asn Leu Lys Ile Asn Gln Tyr Leu
225                 230                 235                 240

Asp Leu Leu Glu Glu Lys Ile Ile Lys Lys Ser Ile Ser Tyr Tyr Asn
                245                 250                 255

Pro Asn Lys Leu Tyr Phe Arg Asp Ile Leu Glu Leu Lys Ser Lys Lys
            260                 265                 270

Ile Phe Asn Leu Phe
        275
```

<210> SEQ ID NO 7
<211> LENGTH: 834

<210> SEQ ID NO 8
<211> LENGTH: 277
<212> TYPE: PRT
<213> ORGANISM: Campylobacter jejuni
<220> FEATURE:
<221> NAME/KEY: MISC_FEATURE
<223> OTHER INFORMATION: strain ATCC 43432, HS:4, Orf 11 sialate-O-acetyltransferase (SOAT)

<400> SEQUENCE: 8

```
<212> TYPE: DNA
<213> ORGANISM: Campylobacter jejuni
<220> FEATURE:
<221> NAME/KEY: misc_feature
<223> OTHER INFORMATION: strain ATCC 43432, HS:4, Orf 11 sialate-O-
      acetyltransferase(SOAT)

<400> SEQUENCE: 7
atggaaaaaa taaccttaaa atgcaataaa aatatattaa atttattaaa gcaatataat      60
atttatacaa aaacttacat agaaaatcct agaagatttt caagactaaa aaccaaagat     120
tttataacca ttccattgga aaacaatcaa ttagagagtg tggctgggct ggggatagaa     180
gaatattatg cttttaaatt tagcaatatc ttacatgaaa tgggttcatt ttcttttagc     240
ggatcttttc tacctcatta tgcaaaagtt ggaaggtatt gttcaattgc tgatggggtt     300
tctatgttta actttcaaca ccctatggat agaatcagca ctgcaagttt tacctatgaa     360
acaaatcata gttttattaa caatgcttgt caaaatcaca tcaacaaaac atttcctata     420
gttaaccata atccaagctc atcaataacg catttaatta tacaagatga tgtttggata     480
ggaaaagatg ttttgcttaa acagggtatc acacttggga ctggatgtgt cataggacaa     540
agagctgtag ttactaaaga tgtaccacct tatgctatag ttgcaggaat tccagccaaa     600
attatcaaat atagatttaa taaaaaaaca atagaaagat tattaaaaat tcaatggtgg     660
aaatatcatt tgctgatttt ttatgatatt gatcttaatt taaaaataaa ccaatatctt     720
gacctactag aagaaaaaat cataaaaaaa tcaatttcct actataatcc aaataaactt     780
tattttagag atattttaga actaaaatca aaaaaatttt ttaatctatt ttaa           834
```

Met Glu Lys Ile Thr Leu Lys Cys Asn Lys Asn Ile Leu Asn Leu Leu
1               5                   10                  15

Lys Gln Tyr Asn Ile Tyr Thr Lys Thr Tyr Ile Glu Asn Pro Arg Arg
            20                  25                  30

Phe Ser Arg Leu Lys Thr Lys Asp Phe Ile Thr Ile Pro Leu Glu Asn
        35                  40                  45

Asn Gln Leu Glu Ser Val Ala Gly Leu Gly Ile Glu Tyr Tyr Ala
    50                  55                  60

Phe Lys Phe Ser Asn Ile Leu His Glu Met Gly Ser Phe Ser Phe Ser
65                  70                  75                  80

Gly Ser Phe Leu Pro His Tyr Ala Lys Val Gly Arg Tyr Cys Ser Ile
                85                  90                  95

Ala Asp Gly Val Ser Met Phe Asn Phe Gln His Pro Met Asp Arg Ile
            100                 105                 110

Ser Thr Ala Ser Phe Thr Tyr Glu Thr Asn His Ser Phe Ile Asn Asn
        115                 120                 125

Ala Cys Gln Asn His Ile Asn Lys Thr Phe Pro Ile Val Asn His Asn
    130                 135                 140

Pro Ser Ser Ser Ile Thr His Leu Ile Ile Gln Asp Asp Val Trp Ile
145                 150                 155                 160

Gly Lys Asp Val Leu Leu Lys Gln Gly Ile Thr Leu Gly Thr Gly Cys
                    165                 170                 175

Val Ile Gly Gln Arg Ala Val Val Thr Lys Asp Val Pro Pro Tyr Ala
            180                 185                 190

Ile Val Ala Gly Ile Pro Ala Lys Ile Ile Lys Tyr Arg Phe Asn Lys
        195                 200                 205

Lys Thr Ile Glu Arg Leu Leu Lys Ile Gln Trp Trp Lys Tyr His Phe
    210                 215                 220

Ala Asp Phe Tyr Asp Ile Asp Leu Asn Leu Lys Ile Asn Gln Tyr Leu
225                 230                 235                 240

Asp Leu Leu Glu Glu Lys Ile Ile Lys Lys Ser Ile Ser Tyr Tyr Asn
                245                 250                 255

Pro Asn Lys Leu Tyr Phe Arg Asp Ile Leu Glu Leu Lys Ser Lys Lys
            260                 265                 270

Ile Phe Asn Leu Phe
            275

<210> SEQ ID NO 9
<211> LENGTH: 831
<212> TYPE: DNA
<213> ORGANISM: Campylobacter jejuni
<220> FEATURE:
<221> NAME/KEY: misc_feature
<223> OTHER INFORMATION: strain ATCC 43438, HS:10, Orf 11 sialate-O-
      acetyltransferase (SOAT)

<400> SEQUENCE: 9
atggaaaaaa taaccttaaa atgcaataaa aatatattaa atttattaaa gcaatataat      60 atttataccaa aaacttacat agaaaatcct agaagatttt caagactaaa aaccaaagat    120
tttataacca ttccattgga aaacaatcga ttagagagtg cggggggggg gatagaagaa    180
tattgtgctt ttaaatttag caatatctta catgaaatgg gttcattttc ttttagcggt    240
tcttttctac tcattacgc aaaagttgga aggtattgtt caattgctga tggggtttct    300
atgtttaact ttcaacatcc tatagataga attagcactg caagttttac ctatgaaaca    360
aatcatagtt ttattaacga tgcttgccaa aatcacatca acaaaacatt tcctatagtt    420
aaccataatc caagctcatc aataacgcat ttaattatac aagatgatgt ttggatagga    480
aaagatgttt tgcttaaaca gggtatcaca cttgggactg gatgtgtcat aggacaaaga    540
gctgtagtta ctaaagatgt accaccttat gctatagttg caggaattcc agccaaaatt    600
atcaaatata gatttaatga aaaaacaata gaaagattat taaaaattca atggtggaga    660
tatcattttg ctgattttta tgatattgat cttaatttaa aaataaacca atatcttgac    720
ctactagaag aaaaaatcat aaaaaaatca atttcctact ataatccaaa taaactttat    780
tttagagata ttttagaact aaaatcaaaa aaaattttta atctattta a               831

<210> SEQ ID NO 10
<211> LENGTH: 276
<212> TYPE: PRT
<213> ORGANISM: Campylobacter jejuni
<220> FEATURE:
<221> NAME/KEY: MISC_FEATURE
<223> OTHER INFORMATION: strain ATCC 43438, HS:10, Orf 11 sialate-O-
      acetyltransferase (SOAT)

<400> SEQUENCE: 10

Met Glu Lys Ile Thr Leu Lys Cys Asn Lys Asn Ile Leu Asn Leu Leu
1               5                   10                  15

```
Lys Gln Tyr Asn Ile Tyr Thr Lys Thr Tyr Ile Glu Asn Pro Arg Arg
                 20                  25                  30

Phe Ser Arg Leu Lys Thr Lys Asp Phe Ile Thr Ile Pro Leu Glu Asn
             35                  40                  45

Asn Arg Leu Glu Ser Ala Gly Gly Ile Glu Glu Tyr Cys Ala Phe
         50                  55                  60

Lys Phe Ser Asn Ile Leu His Glu Met Gly Ser Phe Ser Phe Ser Gly
 65                  70                  75                  80

Ser Phe Leu Pro His Tyr Ala Lys Val Gly Arg Tyr Cys Ser Ile Ala
                 85                  90                  95

Asp Gly Val Ser Met Phe Asn Phe Gln His Pro Ile Asp Arg Ile Ser
            100                 105                 110

Thr Ala Ser Phe Thr Tyr Glu Thr Asn His Ser Phe Ile Asn Asp Ala
            115                 120                 125

Cys Gln Asn His Ile Asn Lys Thr Phe Pro Ile Val Asn His Asn Pro
130                 135                 140

Ser Ser Ser Ile Thr His Leu Ile Ile Gln Asp Asp Val Trp Ile Gly
145                 150                 155                 160

Lys Asp Val Leu Leu Lys Gln Gly Ile Thr Leu Gly Thr Gly Cys Val
                165                 170                 175

Ile Gly Gln Arg Ala Val Val Thr Lys Asp Val Pro Pro Tyr Ala Ile
            180                 185                 190

Val Ala Gly Ile Pro Ala Lys Ile Ile Lys Tyr Arg Phe Asn Glu Lys
            195                 200                 205

Thr Ile Glu Arg Leu Leu Lys Ile Gln Trp Trp Arg Tyr His Phe Ala
210                 215                 220

Asp Phe Tyr Asp Ile Asp Leu Asn Leu Lys Ile Asn Gln Tyr Leu Asp
225                 230                 235                 240

Leu Leu Glu Glu Lys Ile Ile Lys Lys Ser Ile Ser Tyr Tyr Asn Pro
                245                 250                 255

Asn Lys Leu Tyr Phe Arg Asp Ile Leu Glu Leu Lys Ser Lys Lys Ile
            260                 265                 270

Phe Asn Leu Phe
            275

<210> SEQ ID NO 11
<211> LENGTH: 834
<212> TYPE: DNA
<213> ORGANISM: Campylobacter jejuni
<220> FEATURE:
<221> NAME/KEY: misc_feature
<223> OTHER INFORMATION: strain ATCC 43446, HS:19, Orf 11 sialate-O-
      acetyltransferase (SOAT)

<400> SEQUENCE: 11
atggaaaaaa taaccttaaa atgcaataaa aatatattaa atttattaaa gcaatataat      60
atttatacaa aaacttatat agaaaatcct agaagatttt caagactaaa aaccaaagat     120
tttataaccc ttccattgga aaacaatcaa ctagagagtg tagcgggggct ggggatagaa    180 gaatattgtg cttttaaatt tagcaatatc ttacatgaaa tgggttcatt ttcttttagc    240
ggatcttttc tacctcatta tacaaaagtt ggaaggtatt gttcaatttc tgatggggtt   300
tctatgttta actttcaaca tcctatggat agaatcagca ctgcaagttt tacctatgaa   360
acaaatcata gttttattaa cgatgcttgc caaaatcaca tcaacaaaac atttcctata   420
gttaaccata tccaagctct atcaataacg catttaatta tacaagatga tgtttggata   480
```

```
ggaaaagatg ttttgcttaa acagggtatc acacttggga ctggatgtgt cataggacaa      540
agagctgtag ttactaaaga tgtaccacct tatgctatag ttgcaggaat tccagccaaa      600
attatcaaat atagatttga tgaaaaaaca atagaaagat tattaaaaat tcaatggtgg      660
aaatatcatt ttgctgattt ttatgatatt gatcttaatt taaaaataaa ccaatatctt      720
gacctactag aagaaaaaat cataaaaaaa tcaatttcct actataatcc aaataaactt      780
tattttagag atattttaga actaaaatca aaaaaatttt ttaatctatt ttaa            834
```

<210> SEQ ID NO 12
<211> LENGTH: 277
<212> TYPE: PRT
<213> ORGANISM: Campylobacter jejuni
<220> FEATURE:
<221> NAME/KEY: MISC_FEATURE
<223> OTHER INFORMATION: strain ATCC 43446, HS:19, Orf 11 sialate-O-
      acetyltransferase (SOAT)

<400> SEQUENCE: 12

```
Met Glu Lys Ile Thr Leu Lys Cys Asn Lys Asn Ile Leu Asn Leu Leu
1               5                   10                  15

Lys Gln Tyr Asn Ile Tyr Thr Lys Thr Tyr Ile Glu Asn Pro Arg Arg
            20                  25                  30

Phe Ser Arg Leu Lys Thr Lys Asp Phe Ile Thr Phe Pro Leu Glu Asn
        35                  40                  45

Asn Gln Leu Glu Ser Val Ala Gly Leu Gly Ile Glu Glu Tyr Cys Ala
    50                  55                  60

Phe Lys Phe Ser Asn Ile Leu His Glu Met Gly Ser Phe Ser Phe Ser
65                  70                  75                  80

Gly Ser Phe Leu Pro His Tyr Thr Lys Val Gly Arg Tyr Cys Ser Ile
                85                  90                  95

Ser Asp Gly Val Ser Met Phe Asn Phe Gln His Pro Met Asp Arg Ile
            100                 105                 110

Ser Thr Ala Ser Phe Thr Tyr Glu Thr Asn His Ser Phe Ile Asn Asp
        115                 120                 125

Ala Cys Gln Asn His Ile Asn Lys Thr Phe Pro Ile Val Asn His Asn
    130                 135                 140

Pro Ser Ser Ser Ile Thr His Leu Ile Ile Gln Asp Asp Val Trp Ile
145                 150                 155                 160

Gly Lys Asp Val Leu Leu Lys Gln Gly Ile Thr Leu Gly Thr Gly Cys
                165                 170                 175

Val Ile Gly Gln Arg Ala Val Val Thr Lys Asp Val Pro Pro Tyr Ala
            180                 185                 190

Ile Val Ala Gly Ile Pro Ala Lys Ile Lys Tyr Arg Phe Asp Glu
        195                 200                 205

Lys Thr Ile Glu Arg Leu Leu Lys Ile Gln Trp Trp Lys Tyr His Phe
    210                 215                 220

Ala Asp Phe Tyr Asp Ile Asp Leu Asn Leu Lys Ile Asn Gln Tyr Leu
225                 230                 235                 240

Asp Leu Leu Glu Glu Lys Ile Ile Lys Lys Ser Ile Ser Tyr Tyr Asn
                245                 250                 255

Pro Asn Lys Leu Tyr Phe Arg Asp Ile Leu Glu Leu Lys Ser Lys Lys
            260                 265                 270

Ile Phe Asn Leu Phe
        275
```

<210> SEQ ID NO 13
<211> LENGTH: 834
<212> TYPE: DNA
<213> ORGANISM: Campylobacter jejuni
<220> FEATURE:
<221> NAME/KEY: misc_feature
<223> OTHER INFORMATION: strain ATCC 43449, HS:23, Orf 11 sialate-O-
      acetyltransferase (SOAT)

<400> SEQUENCE: 13

```
atggaaaaaa taaccttaaa atgcaataaa aatatattaa atttattaaa gcaatataat    60
atttatacaa aaacttacat agaaaatcct agaagatttt caagactaaa aaccaaagat   120
tttataacca ttccattgaa aaacaatcaa ttagagagtg cggcggggct ggggatagaa   180
gaatattgtg cttttaaatt tagcaatatc ttacatgaaa tgggttcatt ttcttttagc   240
ggatcttttc tacctcatta tgcaaaagtt ggaaggtatt gttcaattgc tgatggggtt   300
tctatgttta actttcaaca ccctatagat agaatcagca ctgcaagttt tacctatgaa   360
acaaatcata gttttattaa cgatgcttgc caaaatcaca tcaacaaaac atttcctata   420
gttaaccata atccaagctc atcaataacg catttaatta tacaagatga tgtttggata   480
ggaaaagatg ttttgcttaa acagggtatc acacttggga ctggatgtgt cataggacaa   540
agagctgtag ttactaaaga tgtaccacct tatgctatag ttgcaggaat tccagccaaa   600
attatcaaat atagatttga tgaaaaaaca atagaaagat tattaaaaat tcaatggtgg   660
agatatcatt ttgctgattt ttatgatatt gatcttaatt taaaaataaa ccaatatctt   720
gacctactag aagaaaaaat cataaaaaaa tcaatttcct actataatcc aaataaactt   780
tattttagag atattttaga actaaaatca aaaaaaattt ttaatctatt ttaa         834
```

<210> SEQ ID NO 14
<211> LENGTH: 277
<212> TYPE: PRT
<213> ORGANISM: Campylobacter jejuni
<220> FEATURE:
<221> NAME/KEY: MISC_FEATURE
<223> OTHER INFORMATION: strain ATCC 43449, HS:23, Orf 11 sialate-O-
      acetyltransferase (SOAT)

<400> SEQUENCE: 14

```
Met Glu Lys Ile Thr Leu Lys Cys Asn Lys Asn Ile Leu Asn Leu Leu
1               5                   10                  15

Lys Gln Tyr Asn Ile Tyr Thr Lys Thr Tyr Ile Glu Asn Pro Arg Arg
            20                  25                  30

Phe Ser Arg Leu Lys Thr Lys Asp Phe Ile Thr Ile Pro Leu Lys Asn
        35                  40                  45

Asn Gln Leu Glu Ser Ala Ala Gly Leu Gly Ile Glu Glu Tyr Cys Ala
    50                  55                  60

Phe Lys Phe Ser Asn Ile Leu His Glu Met Gly Ser Phe Ser Phe Ser
65                  70                  75                  80

Gly Ser Phe Leu Pro His Tyr Ala Lys Val Gly Arg Tyr Cys Ser Ile
                85                  90                  95

Ala Asp Gly Val Ser Met Phe Asn Phe Gln His Pro Ile Asp Arg Ile
            100                 105                 110

Ser Thr Ala Ser Phe Thr Tyr Glu Thr Asn His Ser Phe Ile Asn Asp
        115                 120                 125

Ala Cys Gln Asn His Ile Asn Lys Thr Phe Pro Ile Val Asn His Asn
    130                 135                 140

Pro Ser Ser Ser Ile Thr His Leu Ile Ile Gln Asp Asp Val Trp Ile
```

Gly Lys Asp Val Leu Leu Lys Gln Gly Ile Thr Leu Gly Thr Gly Cys
145                 150                 155                 160

Val Ile Gly Gln Arg Ala Val Val Thr Lys Asp Val Pro Pro Tyr Ala
                165                 170                 175

Ile Val Ala Gly Ile Pro Ala Lys Ile Ile Lys Tyr Arg Phe Asp Glu
            180                 185                 190

Lys Thr Ile Glu Arg Leu Leu Lys Ile Gln Trp Trp Arg Tyr His Phe
        195                 200                 205

Ala Asp Phe Tyr Asp Ile Asp Leu Asn Leu Lys Ile Asn Gln Tyr Leu
    210                 215                 220

Asp Leu Leu Glu Glu Lys Ile Ile Lys Lys Ser Ile Ser Tyr Asn
225                 230                 235                 240

Pro Asn Lys Leu Tyr Phe Arg Asp Ile Leu Glu Leu Lys Ser Lys Lys
                245                 250                 255

Ile Phe Asn Leu Phe
        260                 265                 270

275

<210> SEQ ID NO 15
<211> LENGTH: 834
<212> TYPE: DNA
<213> ORGANISM: Campylobacter jejuni
<220> FEATURE:
<221> NAME/KEY: misc_feature
<223> OTHER INFORMATION: strain ATCC 43456, HS:36, Orf 11 sialate-O-
      acetyltransferase (SOAT)

<400> SEQUENCE: 15
atggaaaaaa taaccttaaa atgcaataaa aatatattaa atttattaaa gcaatataat      60
atttatacaa aaacttacat agaaaatcct agaagatttt caagactaaa aaccaaagat     120
tttataacca ttccattgaa aaacaatcaa ttagagagtg cggcggggct ggggatagaa     180
gaatattgtg cttttaaatt tagcaatatc ttacatgaaa tgggttcatt ttcttttagc     240
ggatcttttc tacctcatta tgcaaaagtt gaaaggtatt gttcaattgc tgatggggtt     300
tctatgttta actttcaaca ccctatagat agaatcagca ctgcaagttt tacctatgaa     360
acaaatcata gttttattaa cgatgcttgc caaaatcaca tcaacaaaac atttcctata     420
gttaaccata atccaagctc atcaataacg catttaatta tacaagatga tgtttggata     480
ggaaaagatg ttttgcttaa acagggtatc acacttggga ctggatgtgt cataggacaa     540
agagctgtag ttactaaaga tgtaccacct tatgctatag ttgcaggaat tccagccaaa     600
attatcaaat atagatttga tgaaaaaaca atagaaagat tattaaaaat tcaatggtgg     660
agatatcatt ttgctgattt ttatgatatt gatcttaatt taaaaataaa ccaatatctt     720
gacctactag aagaaaaaat cataaaaaaa tcaatttcct actataatcc aaataaactt     780
tattttagag atattttaga actaaaatca aaaaaaattt ttaatctatt ttaa           834

<210> SEQ ID NO 16
<211> LENGTH: 277
<212> TYPE: PRT
<213> ORGANISM: Campylobacter jejuni
<220> FEATURE:
<221> NAME/KEY: MISC_FEATURE
<223> OTHER INFORMATION: strain ATCC 43456, HS:36, Orf 11 sialate-O-
      acetyltransferase (SOAT)

<400> SEQUENCE: 16

Met Glu Lys Ile Thr Leu Lys Cys Asn Lys Asn Ile Leu Asn Leu Leu

```
        1               5                   10                  15
    Lys Gln Tyr Asn Ile Tyr Thr Lys Thr Tyr Ile Glu Asn Pro Arg Arg
                    20                  25                  30

Phe Ser Arg Leu Lys Thr Lys Asp Phe Ile Thr Ile Pro Leu Lys Asn
                    35                  40                  45

Asn Gln Leu Glu Ser Ala Ala Gly Leu Gly Ile Glu Glu Tyr Cys Ala
                    50                  55                  60

Phe Lys Phe Ser Asn Ile Leu His Glu Met Gly Ser Phe Ser Phe Ser
     65                  70                  75                  80

Gly Ser Phe Leu Pro His Tyr Ala Lys Val Glu Arg Tyr Cys Ser Ile
                        85                  90                  95

Ala Asp Gly Val Ser Met Phe Asn Phe Gln His Pro Ile Asp Arg Ile
                    100                 105                 110

Ser Thr Ala Ser Phe Thr Tyr Glu Thr Asn His Ser Phe Ile Asn Asp
                    115                 120                 125

Ala Cys Gln Asn His Ile Asn Lys Thr Phe Pro Ile Val Asn His Asn
                    130                 135                 140

Pro Ser Ser Ile Thr His Leu Ile Ile Gln Asp Asp Val Trp Ile
    145                 150                 155                 160

Gly Lys Asp Val Leu Leu Lys Gln Gly Ile Thr Leu Gly Thr Gly Cys
                        165                 170                 175

Val Ile Gly Gln Arg Ala Val Val Thr Lys Asp Val Pro Pro Tyr Ala
                    180                 185                 190

Ile Val Ala Gly Ile Pro Ala Lys Ile Lys Tyr Arg Phe Asp Glu
                    195                 200                 205

Lys Thr Ile Glu Arg Leu Leu Lys Ile Gln Trp Trp Arg Tyr His Phe
                    210                 215                 220

Ala Asp Phe Tyr Asp Ile Asp Leu Asn Leu Lys Ile Asn Gln Tyr Leu
    225                 230                 235                 240

Asp Leu Leu Glu Glu Lys Ile Ile Lys Lys Ser Ile Ser Tyr Asn
                        245                 250                 255

Pro Asn Lys Leu Tyr Phe Arg Asp Ile Leu Glu Leu Lys Ser Lys Lys
                        260                 265                 270

Ile Phe Asn Leu Phe
                    275

<210> SEQ ID NO 17
<211> LENGTH: 192
<212> TYPE: DNA
<213> ORGANISM: Campylobacter jejuni
<220> FEATURE:
<221> NAME/KEY: misc_feature
<223> OTHER INFORMATION: strain ATCC 43460, HS:41, Orf 11 sialate-O-
      acetyltransferase (SOAT)

<400> SEQUENCE: 17
atggaaaaaa taaccttaaa atgcaataaa aatatattaa atttattaaa gcaatataat      60
atttataaca aaacttacat agaaaatcct agaagatttt caagactaaa aaccaaagat     120
tttataacca ttccattgga aaacaatcaa ttagagagtg cgggggggga tagaagaata     180
ttgtgctttt aa                                                         192

<210> SEQ ID NO 18
<211> LENGTH: 63
<212> TYPE: PRT
<213> ORGANISM: Campylobacter jejuni
<220> FEATURE:
```

<221> NAME/KEY: MISC_FEATURE
<223> OTHER INFORMATION: strain ATCC 43460, HS:41, Orf 11 sialate-O-
      acetyltransferase (SOAT)

<400> SEQUENCE: 18

Met Glu Lys Ile Thr Leu Lys Cys Asn Lys Asn Ile Leu Asn Leu Leu
1               5                   10                  15

Lys Gln Tyr Asn Ile Tyr Thr Lys Thr Tyr Ile Glu Asn Pro Arg Arg
            20                  25                  30

Phe Ser Arg Leu Lys Thr Lys Asp Phe Ile Thr Ile Pro Leu Glu Asn
        35                  40                  45

Asn Gln Leu Glu Ser Ala Gly Gly Asp Arg Arg Ile Leu Cys Phe
    50                  55                  60

<210> SEQ ID NO 19
<211> LENGTH: 277
<212> TYPE: PRT
<213> ORGANISM: Artificial Sequence
<220> FEATURE:
<223> OTHER INFORMATION: Description of Artificial Sequence:
      Campylobacter jejuni Orf 11 sialate-O-acetyltransferase (SOAT)
      consensus sequence

<400> SEQUENCE: 19

Met Glu Lys Ile Thr Leu Lys Cys Asn Lys Asn Ile Leu Asn Leu Leu
1               5                   10                  15

Lys Gln Tyr Asn Ile Tyr Thr Lys Thr Tyr Ile Glu Asn Pro Arg Arg
            20                  25                  30

Phe Ser Arg Leu Lys Thr Lys Asp Phe Ile Thr Ile Pro Leu Glu Asn
        35                  40                  45

Asn Gln Leu Glu Ser Ala Ala Gly Leu Gly Ile Glu Glu Tyr Cys Ala
    50                  55                  60

Phe Lys Phe Ser Asn Ile Leu His Glu Met Gly Ser Phe Ser Phe Ser
65                  70                  75                  80

Gly Ser Phe Leu Pro His Tyr Ala Lys Val Gly Arg Tyr Cys Ser Ile
                85                  90                  95

Ala Asp Gly Val Ser Met Phe Asn Phe Gln His Pro Met Asp Arg Ile
            100                 105                 110

Ser Thr Ala Ser Phe Thr Tyr Glu Thr Asn His Ser Phe Ile Asn Asp
        115                 120                 125

Ala Cys Gln Asn His Ile Asn Lys Thr Phe Pro Ile Val Asn His Asn
    130                 135                 140

Pro Ser Ser Ser Ile Thr His Leu Ile Ile Gln Asp Asp Val Trp Ile
145                 150                 155                 160

Gly Lys Asp Val Leu Leu Lys Gln Gly Ile Thr Leu Gly Thr Gly Cys
                165                 170                 175

Val Ile Gly Gln Arg Ala Val Val Thr Lys Asp Val Pro Pro Tyr Ala
            180                 185                 190

Ile Val Ala Gly Ile Pro Ala Lys Ile Ile Lys Tyr Arg Phe Asp Glu
        195                 200                 205

Lys Thr Ile Glu Arg Leu Leu Lys Ile Gln Trp Trp Lys Tyr His Phe
    210                 215                 220

Ala Asp Phe Tyr Asp Ile Asp Leu Asn Leu Lys Ile Asn Gln Tyr Leu
225                 230                 235                 240

Asp Leu Leu Glu Glu Lys Ile Ile Lys Lys Ser Ile Ser Tyr Tyr Asn
                245                 250                 255

Pro Asn Lys Leu Tyr Phe Arg Asp Ile Leu Glu Leu Lys Ser Lys Lys

Ile Phe Asn Leu Phe
            275

<210> SEQ ID NO 20
<211> LENGTH: 139
<212> TYPE: PRT
<213> ORGANISM: Campylobacter jejuni
<220> FEATURE:
<221> NAME/KEY: MISC_FEATURE
<223> OTHER INFORMATION: amino acid residues 78-216 of strain ATCC
      43438, HS:10, Orf 11 sialate-O-acetyltransferase (SOAT)

<400> SEQUENCE: 20

Phe Ser Gly Ser Phe Leu Pro His Tyr Ala Lys Val Gly Arg Tyr Cys
1               5                   10                  15

Ser Ile Ala Asp Gly Val Ser Met Phe Asn Phe Gln His Pro Ile Asp
            20                  25                  30

Arg Ile Ser Thr Ala Ser Phe Thr Tyr Glu Thr Asn His Ser Phe Ile
        35                  40                  45

Asn Asp Ala Cys Gln Asn His Ile Asn Lys Thr Phe Pro Ile Val Asn
    50                  55                  60

His Asn Pro Ser Ser Ser Ile Thr His Leu Ile Ile Gln Asp Asp Val
65                  70                  75                  80

Trp Ile Gly Lys Asp Val Leu Leu Lys Gln Gly Ile Thr Leu Gly Thr
                85                  90                  95

Gly Cys Val Ile Gly Gln Arg Ala Val Val Thr Lys Asp Val Pro Pro
            100                 105                 110

Tyr Ala Ile Val Ala Gly Ile Pro Ala Lys Ile Ile Lys Tyr Arg Phe
        115                 120                 125

Asn Glu Lys Thr Ile Glu Arg Leu Leu Lys Ile
    130                 135

<210> SEQ ID NO 21
<211> LENGTH: 132
<212> TYPE: PRT
<213> ORGANISM: Artificial Sequence
<220> FEATURE:
<223> OTHER INFORMATION: Description of Artificial Sequence:amino acid
      residues 59-190 of WbbJ, Acetyltransferase (isoleucine patch
      superfamily) domain, gnl/CDD/9985 COG0110

<400> SEQUENCE: 21

Val Arg Ile Asp Leu Gly Glu Lys Asn Leu Thr Ile Gly Asp Leu Cys
1               5                   10                  15

Phe Ile Gly Val Asn Val Val Ile Leu Val Gly Glu Gly Ile Thr Ile
            20                  25                  30

Gly Asp Asn Val Val Val Gly Pro Asn Val Thr Ile Tyr Thr Asn Ser
        35                  40                  45

His Pro Gly Asp Phe Val Thr Ala Asn Ile Gly Ala Leu Val Gly Ala
    50                  55                  60

Gly Pro Val Thr Ile Gly Glu Asp Val Trp Ile Gly Ala Gly Ala Val
65                  70                  75                  80

Ile Leu Pro Gly Val Thr Ile Gly Glu Gly Ala Val Ile Gly Ala Gly
                85                  90                  95

Ser Val Val Thr Lys Asp Val Pro Pro Tyr Gly Ile Val Ala Gly Asn
            100                 105                 110

Pro Ala Arg Val Ile Arg Lys Arg Asp Val Val Ala Lys Ile Gly Val
        115                 120                 125

```
Leu Leu Ala Pro
    130

<210> SEQ ID NO 22
<211> LENGTH: 333
<212> TYPE: PRT
<213> ORGANISM: Artificial Sequence
<220> FEATURE:
<223> OTHER INFORMATION: Description of Artficial Sequence: consensus
      sequence for E. coli strain RS164 serotype K1 NeuO polysialic acid
      O-acetyltransferase, N. meningitidis serogroup Y OatY ORF and C.
      jejuni strain ATCC 43438, Orf 11 sialate-O-acetyltransferase
<220> FEATURE:
<221> NAME/KEY: MOD_RES
<222> LOCATION: (41)..(41)
<223> OTHER INFORMATION: Xaa = Thr or Met
<220> FEATURE:
<221> NAME/KEY: MOD_RES
<222> LOCATION: (43)..(43)
<223> OTHER INFORMATION: Xaa = Asp or Lys
<220> FEATURE:
<221> NAME/KEY: MOD_RES
<222> LOCATION: (44)..(44)
<223> OTHER INFORMATION: Xaa = Ser or Ile
<220> FEATURE:
<221> NAME/KEY: MOD_RES
<222> LOCATION: (45)..(45)
<223> OTHER INFORMATION: Xaa = Arg or Thr
<220> FEATURE:
<221> NAME/KEY: MOD_RES
<222> LOCATION: (49)..(49)
<223> OTHER INFORMATION: Xaa = Gln, His or Asn
<220> FEATURE:
<221> NAME/KEY: MOD_RES
<222> LOCATION: (50)..(50)
<223> OTHER INFORMATION: Xaa = Asp, Met or Lys
<220> FEATURE:
<221> NAME/KEY: MOD_RES
<222> LOCATION: (51)..(51)
<223> OTHER INFORMATION: Xaa = Ser, Tyr or Asn
<220> FEATURE:
<221> NAME/KEY: MOD_RES
<222> LOCATION: (52)..(52)
<223> OTHER INFORMATION: Xaa = Arg, Ser or Ile
<220> FEATURE:
<221> NAME/KEY: MOD_RES
<222> LOCATION: (54)..(54)
<223> OTHER INFORMATION: Xaa = Lys, Gln or Asn
<220> FEATURE:
<221> NAME/KEY: MOD_RES
<222> LOCATION: (55)..(55)
<223> OTHER INFORMATION: Xaa = Thr, Gly or Leu
<220> FEATURE:
<221> NAME/KEY: MOD_RES
<222> LOCATION: (56)..(56)
<223> OTHER INFORMATION: Xaa = Gln, Ile or Leu
<220> FEATURE:
<221> NAME/KEY: MOD_RES
<222> LOCATION: (57)..(57)
<223> OTHER INFORMATION: Xaa = Asp, Asn or Lys
<220> FEATURE:
<221> NAME/KEY: MOD_RES
<222> LOCATION: (58)..(58)
<223> OTHER INFORMATION: Xaa = Ser, Asn or Gln
<220> FEATURE:
<221> NAME/KEY: MOD_RES
<222> LOCATION: (59)..(59)
<223> OTHER INFORMATION: Xaa = Arg, Thr or Tyr
<220> FEATURE:
<221> NAME/KEY: MOD_RES
<222> LOCATION: (60)..(60)
<223> OTHER INFORMATION: Xaa = Leu, Ile or Asn
<220> FEATURE:
<221> NAME/KEY: MOD_RES
<222> LOCATION: (61)..(61)
<223> OTHER INFORMATION: Xaa = Lys, Asn or Ile
<220> FEATURE:
```

-continued

```
<221> NAME/KEY: MOD_RES
<222> LOCATION: (62)..(62)
<223> OTHER INFORMATION: Xaa = Thr, Ile or Tyr
<220> FEATURE:
<221> NAME/KEY: MOD_RES
<222> LOCATION: (63)..(63)
<223> OTHER INFORMATION: Xaa = Gln, Ser or Thr
<220> FEATURE:
<221> NAME/KEY: MOD_RES
<222> LOCATION: (64)..(64)
<223> OTHER INFORMATION: Xaa = Asp, Thr or Lys
<220> FEATURE:
<221> NAME/KEY: MOD_RES
<222> LOCATION: (66)..(66)
<223> OTHER INFORMATION: Xaa = Arg, Ser or Tyr
<220> FEATURE:
<221> NAME/KEY: MOD_RES
<222> LOCATION: (68)..(68)
<223> OTHER INFORMATION: Xaa = Lys, Thr or Glu
<220> FEATURE:
<221> NAME/KEY: MOD_RES
<222> LOCATION: (70)..(70)
<223> OTHER INFORMATION: Xaa = Gln, Ala or Pro
<220> FEATURE:
<221> NAME/KEY: MOD_RES
<222> LOCATION: (71)..(71)
<223> OTHER INFORMATION: Xaa = Asp, Thr or Arg
<220> FEATURE:
<221> NAME/KEY: MOD_RES
<222> LOCATION: (72)..(72)
<223> OTHER INFORMATION: Xaa = Ser, Gln or Arg
<220> FEATURE:
<221> NAME/KEY: MOD_RES
<222> LOCATION: (76)..(76)
<223> OTHER INFORMATION: Xaa = Asp, Ile or Leu
<220> FEATURE:
<221> NAME/KEY: MOD_RES
<222> LOCATION: (77)..(77)
<223> OTHER INFORMATION: Xaa = Asp, Gly or Lys
<220> FEATURE:
<221> NAME/KEY: MOD_RES
<222> LOCATION: (79)..(79)
<223> OTHER INFORMATION: Xaa = Gly, Asn or Lys
<220> FEATURE:
<221> NAME/KEY: MOD_RES
<222> LOCATION: (80)..(80)
<223> OTHER INFORMATION: Xaa = Ser or Asp
<220> FEATURE:
<221> NAME/KEY: MOD_RES
<222> LOCATION: (82)..(82)
<223> OTHER INFORMATION: Xaa = Gly or Ile
<220> FEATURE:
<221> NAME/KEY: MOD_RES
<222> LOCATION: (84)..(84)
<223> OTHER INFORMATION: Xaa = Val, Ser or Ile
<220> FEATURE:
<221> NAME/KEY: MOD_RES
<222> LOCATION: (85)..(85)
<223> OTHER INFORMATION: Xaa = Phe, Val or Pro
<220> FEATURE:
<221> NAME/KEY: MOD_RES
<222> LOCATION: (86)..(86)
<223> OTHER INFORMATION: Xaa = Val, Tyr or Leu
<220> FEATURE:
<221> NAME/KEY: MOD_RES
<222> LOCATION: (87)..(87)
<223> OTHER INFORMATION: Xaa = Cys, Ile or Glu
<220> FEATURE:
<221> NAME/KEY: MOD_RES
<222> LOCATION: (90)..(90)
<223> OTHER INFORMATION: Xaa = Leu, Asn or Arg
<220> FEATURE:
<221> NAME/KEY: MOD_RES
<222> LOCATION: (91)..(91)
<223> OTHER INFORMATION: Xaa = Val, Cys or Leu
<220> FEATURE:
<221> NAME/KEY: MOD_RES
<222> LOCATION: (92)..(92)
<223> OTHER INFORMATION: Xaa = Asn, Lys or Glu
```

```
<220> FEATURE:
<221> NAME/KEY: MOD_RES
<222> LOCATION: (94)..(94)
<223> OTHER INFORMATION: Xaa = Lys, Val or Ala
<220> FEATURE:
<221> NAME/KEY: MOD_RES
<222> LOCATION: (95)..(95)
<223> OTHER INFORMATION: Xaa = Glu, Ser or Gly
<220> FEATURE:
<221> NAME/KEY: MOD_RES
<222> LOCATION: (96)..(96)
<223> OTHER INFORMATION: Xaa = Asn, Ser or Gly
<220> FEATURE:
<221> NAME/KEY: MOD_RES
<222> LOCATION: (97)..(97)
<223> OTHER INFORMATION: Xaa = Lys, Asn or Gly
<220> FEATURE:
<221> NAME/KEY: MOD_RES
<222> LOCATION: (99)..(99)
<223> OTHER INFORMATION: Xaa = Gln, Arg or Glu
<220> FEATURE:
<221> NAME/KEY: MOD_RES
<222> LOCATION: (100)..(100)
<223> OTHER INFORMATION: Xaa = Phe, Leu or Glu
<220> FEATURE:
<221> NAME/KEY: MOD_RES
<222> LOCATION: (101)..(101)
<223> OTHER INFORMATION: Xaa = Asn, Lys or Tyr
<220> FEATURE:
<221> NAME/KEY: MOD_RES
<222> LOCATION: (105)..(105)
<223> OTHER INFORMATION: Xaa = Asn, Ile or Lys
<220> FEATURE:
<221> NAME/KEY: MOD_RES
<222> LOCATION: (106)..(106)
<223> OTHER INFORMATION: Xaa = Lys, Thr or Phe
<220> FEATURE:
<221> NAME/KEY: MOD_RES
<222> LOCATION: (108)..(108)
<223> OTHER INFORMATION: Xaa = Ile, Phe or Asn
<220> FEATURE:
<221> NAME/KEY: MOD_RES
<222> LOCATION: (110)..(110)
<223> OTHER INFORMATION: Xaa = Glu, Ala or Leu
<220> FEATURE:
<221> NAME/KEY: MOD_RES
<222> LOCATION: (115)..(115)
<223> OTHER INFORMATION: Xaa = Cys, Asn or Ser
<220> FEATURE:
<221> NAME/KEY: MOD_RES
<222> LOCATION: (116)..(116)
<223> OTHER INFORMATION: Xaa = Arg, Met or Phe
<220> FEATURE:
<221> NAME/KEY: MOD_RES
<222> LOCATION: (117)..(117)
<223> OTHER INFORMATION: Xaa = Trp, Gly or Ser
<220> FEATURE:
<221> NAME/KEY: MOD_RES
<222> LOCATION: (119)..(119)
<223> OTHER INFORMATION: Xaa = Thr, Val or Ser
<220> FEATURE:
<221> NAME/KEY: MOD_RES
<222> LOCATION: (120)..(120)
<223> OTHER INFORMATION: Xaa = Val, Cys or Gly
<220> FEATURE:
<221> NAME/KEY: MOD_RES
<222> LOCATION: (123)..(123)
<223> OTHER INFORMATION: Xaa = Arg, His or Leu
<220> FEATURE:
<221> NAME/KEY: MOD_RES
<222> LOCATION: (124)..(124)
<223> OTHER INFORMATION: Xaa = Gly, Ser or Pro
<220> FEATURE:
<221> NAME/KEY: MOD_RES
<222> LOCATION: (126)..(126)
<223> OTHER INFORMATION: Xaa = Asn or Tyr
<220> FEATURE:
<221> NAME/KEY: MOD_RES
<222> LOCATION: (144)..(144)
```

```
<223> OTHER INFORMATION: Xaa = Thr or Lys
<220> FEATURE:
<221> NAME/KEY: MOD_RES
<222> LOCATION: (145)..(145)
<223> OTHER INFORMATION: Xaa = Lys or Val
<220> FEATURE:
<221> NAME/KEY: MOD_RES
<222> LOCATION: (148)..(148)
<223> OTHER INFORMATION: Xaa = Lys or Tyr
<220> FEATURE:
<221> NAME/KEY: MOD_RES
<222> LOCATION: (149)..(149)
<223> OTHER INFORMATION: Xaa = Val, Leu or Cys
<220> FEATURE:
<221> NAME/KEY: MOD_RES
<222> LOCATION: (150)..(150)
<223> OTHER INFORMATION: Xaa = Ile, Gln or Ser
<220> FEATURE:
<221> NAME/KEY: MOD_RES
<222> LOCATION: (152)..(152)
<223> OTHER INFORMATION: Xaa = Gly, Gln or Ala
<220> FEATURE:
<221> NAME/KEY: MOD_RES
<222> LOCATION: (153)..(153)
<223> OTHER INFORMATION: Xaa = Arg, Ala or Asp
<220> FEATURE:
<221> NAME/KEY: MOD_RES
<222> LOCATION: (154)..(154)
<223> OTHER INFORMATION: Xaa = Arg, Lys or Gly
<220> FEATURE:
<221> NAME/KEY: MOD_RES
<222> LOCATION: (161)..(161)
<223> OTHER INFORMATION: Xaa = Phe, Glu or Gln
<220> FEATURE:
<221> NAME/KEY: MOD_RES
<222> LOCATION: (162)..(162)
<223> OTHER INFORMATION: Xaa = Glu, Ile or His
<220> FEATURE:
<221> NAME/KEY: MOD_RES
<222> LOCATION: (163)..(163)
<223> OTHER INFORMATION: Xaa = Val, Thr or Pro
<220> FEATURE:
<221> NAME/KEY: MOD_RES
<222> LOCATION: (165)..(165)
<223> OTHER INFORMATION: Xaa = Thr, Ala or Asp
<220> FEATURE:
<221> NAME/KEY: MOD_RES
<222> LOCATION: (166)..(166)
<223> OTHER INFORMATION: Xaa = Asp, Glu or Lys
<220> FEATURE:
<221> NAME/KEY: MOD_RES
<222> LOCATION: (168)..(168)
<223> OTHER INFORMATION: Xaa = Cys, Gly or Ser
<220> FEATURE:
<221> NAME/KEY: MOD_RES
<222> LOCATION: (169)..(169)
<223> OTHER INFORMATION: Xaa = Asn, Lys or Thr
<220> FEATURE:
<221> NAME/KEY: MOD_RES
<222> LOCATION: (170)..(170)
<223> OTHER INFORMATION: Xaa = Val, Ile or Ala
<220> FEATURE:
<221> NAME/KEY: MOD_RES
<222> LOCATION: (174)..(174)
<223> OTHER INFORMATION: Xaa = His, Lys or Tyr
<220> FEATURE:
<221> NAME/KEY: MOD_RES
<222> LOCATION: (178)..(178)
<223> OTHER INFORMATION: Xaa = Ile, Leu or His
<220> FEATURE:
<221> NAME/KEY: MOD_RES
<222> LOCATION: (180)..(180)
<223> OTHER INFORMATION: Xaa = Arg, His or Phe
<220> FEATURE:
<221> NAME/KEY: MOD_RES
<222> LOCATION: (181)..(181)
<223> OTHER INFORMATION: Xaa = Asp, Gly or Ile
<220> FEATURE:
<221> NAME/KEY: MOD_RES
```

```
<222> LOCATION: (182)..(182)
<223> OTHER INFORMATION: Xaa = Val, Tyr or Asn
<220> FEATURE:
<221> NAME/KEY: MOD_RES
<222> LOCATION: (183)..(183)
<223> OTHER INFORMATION: Xaa = Ile, Glu or Asp
<220> FEATURE:
<221> NAME/KEY: MOD_RES
<222> LOCATION: (184)..(184)
<223> OTHER INFORMATION: Xaa = Leu, Ile or Ala
<220> FEATURE:
<221> NAME/KEY: MOD_RES
<222> LOCATION: (186)..(186)
<223> OTHER INFORMATION: Xaa = Ala, Asn or Gln
<220> FEATURE:
<221> NAME/KEY: MOD_RES
<222> LOCATION: (187)..(187)
<223> OTHER INFORMATION: Xaa = Ser, Thr or Asn
<220> FEATURE:
<221> NAME/KEY: MOD_RES
<222> LOCATION: (189)..(189)
<223> OTHER INFORMATION: Xaa = Gly, Met or Ile
<220> FEATURE:
<221> NAME/KEY: MOD_RES
<222> LOCATION: (194)..(194)
<223> OTHER INFORMATION: Xaa = Asp, Ser or Pro
<220> FEATURE:
<221> NAME/KEY: MOD_RES
<222> LOCATION: (196)..(196)
<223> OTHER INFORMATION: Xaa = His, Glu or Val
<220> FEATURE:
<221> NAME/KEY: MOD_RES
<222> LOCATION: (198)..(198)
<223> OTHER INFORMATION: Xaa = Lys, Gly or His
<220> FEATURE:
<221> NAME/KEY: MOD_RES
<222> LOCATION: (199)..(199)
<223> OTHER INFORMATION: Xaa = Lys, Glu or Asn
<220> FEATURE:
<221> NAME/KEY: MOD_RES
<222> LOCATION: (203)..(203)
<223> OTHER INFORMATION: Xaa = Trp, His or Ser
<220> FEATURE:
<221> NAME/KEY: MOD_RES
<222> LOCATION: (204)..(204)
<223> OTHER INFORMATION: Xaa = Ala, Gly or Ile
<220> FEATURE:
<221> NAME/KEY: MOD_RES
<222> LOCATION: (207)..(207)
<223> OTHER INFORMATION: Xaa = Ile, Val or Leu
<220> FEATURE:
<221> NAME/KEY: MOD_RES
<222> LOCATION: (210)..(210)
<223> OTHER INFORMATION: Xaa = Ser, Gly or Gln
<220> FEATURE:
<221> NAME/KEY: MOD_RES
<222> LOCATION: (211)..(211)
<223> OTHER INFORMATION: Xaa = Ser, Asn or Asp
<220> FEATURE:
<221> NAME/KEY: MOD_RES
<222> LOCATION: (212)..(212)
<223> OTHER INFORMATION: Xaa = Tyr, His or Asp
<220> FEATURE:
<221> NAME/KEY: MOD_RES
<222> LOCATION: (215)..(215)
<223> OTHER INFORMATION: Xaa = Val, Leu or Ile
<220> FEATURE:
<221> NAME/KEY: MOD_RES
<222> LOCATION: (220)..(220)
<223> OTHER INFORMATION: Xaa = Ser, Thr or Leu
<220> FEATURE:
<221> NAME/KEY: MOD_RES
<222> LOCATION: (222)..(222)
<223> OTHER INFORMATION: Xaa = Met, Leu or Lys
<220> FEATURE:
<221> NAME/KEY: MOD_RES
<222> LOCATION: (226)..(226)
<223> OTHER INFORMATION: Xaa = Ser, Cys or Thr
<220> FEATURE:
```

```
<221> NAME/KEY: MOD_RES
<222> LOCATION: (227)..(227)
<223> OTHER INFORMATION: Xaa = Val, Ile or Leu
<220> FEATURE:
<221> NAME/KEY: MOD_RES
<222> LOCATION: (229)..(229)
<223> OTHER INFORMATION: Xaa = Ser, Asn or Thr
<220> FEATURE:
<221> NAME/KEY: MOD_RES
<222> LOCATION: (231)..(231)
<223> OTHER INFORMATION: Xaa = Ser, Val or Cys
<220> FEATURE:
<221> NAME/KEY: MOD_RES
<222> LOCATION: (235)..(235)
<223> OTHER INFORMATION: Xaa = Tyr, Ser or Gln
<220> FEATURE:
<221> NAME/KEY: MOD_RES
<222> LOCATION: (236)..(236)
<223> OTHER INFORMATION: Xaa = Gly, His or Arg
<220> FEATURE:
<221> NAME/KEY: MOD_RES
<222> LOCATION: (237)..(237)
<223> OTHER INFORMATION: Xaa = Ser, Thr or Ala
<220> FEATURE:
<221> NAME/KEY: MOD_RES
<222> LOCATION: (247)..(247)
<223> OTHER INFORMATION: Xaa = Met, Asn or Tyr
<220> FEATURE:
<221> NAME/KEY: MOD_RES
<222> LOCATION: (249)..(249)
<223> OTHER INFORMATION: Xaa = Als, Val or Ile
<220> FEATURE:
<221> NAME/KEY: MOD_RES
<222> LOCATION: (249)..(249)
<223> OTHER INFORMATION: Xaa = Ala, Val or Ile
<220> FEATURE:
<221> NAME/KEY: MOD_RES
<222> LOCATION: (250)..(250)
<223> OTHER INFORMATION: Xaa = Ala, Ile or Val
<220> FEATURE:
<221> NAME/KEY: MOD_RES
<222> LOCATION: (253)..(253)
<223> OTHER INFORMATION: Xaa = Asn, Ser or Ile
<220> FEATURE:
<221> NAME/KEY: MOD_RES
<222> LOCATION: (260)..(260)
<223> OTHER INFORMATION: Xaa = Arg, Glu or Tyr
<220> FEATURE:
<221> NAME/KEY: MOD_RES
<222> LOCATION: (274)..(274)
<223> OTHER INFORMATION: Xaa = Ile, Val or Gln
<220> FEATURE:
<221> NAME/KEY: MOD_RES
<222> LOCATION: (276)..(276)
<223> OTHER INFORMATION: Xaa = Ala, Gly or Trp
<220> FEATURE:
<221> NAME/KEY: MOD_RES
<222> LOCATION: (278)..(278)
<223> OTHER INFORMATION: Xaa = Thr, Lys or Tyr
<220> FEATURE:
<221> NAME/KEY: MOD_RES
<222> LOCATION: (279)..(279)
<223> OTHER INFORMATION: Xaa = Asp, Met or His
<220> FEATURE:
<221> NAME/KEY: MOD_RES
<222> LOCATION: (280)..(280)
<223> OTHER INFORMATION: Xaa = Lys, Tyr or Phe
<220> FEATURE:
<221> NAME/KEY: MOD_RES
<222> LOCATION: (282)..(282)
<223> OTHER INFORMATION: Xaa = Glu, Ser or Asp
<220> FEATURE:
<221> NAME/KEY: MOD_RES
<222> LOCATION: (283)..(283)
<223> OTHER INFORMATION: Xaa = Leu, Thr or Phe
<220> FEATURE:
<221> NAME/KEY: MOD_RES
<222> LOCATION: (284)..(284)
<223> OTHER INFORMATION: Xaa = Ile, Met or Tyr
```

```
<220> FEATURE:
<221> NAME/KEY: MOD_RES
<222> LOCATION: (285)..(285)
<223> OTHER INFORMATION: Xaa = Ser, Tyr or Asp
<220> FEATURE:
<221> NAME/KEY: MOD_RES
<222> LOCATION: (288)..(288)
<223> OTHER INFORMATION: Xaa = Lys, Pro or Leu
<220> FEATURE:
<221> NAME/KEY: MOD_RES
<222> LOCATION: (291)..(291)
<223> OTHER INFORMATION: Xaa = Arg, Thr or Lys
<220> FEATURE:
<221> NAME/KEY: MOD_RES
<222> LOCATION: (292)..(292)
<223> OTHER INFORMATION: Xaa = Cys, Leu or Ile
<220> FEATURE:
<221> NAME/KEY: MOD_RES
<222> LOCATION: (294)..(294)
<223> OTHER INFORMATION: Xaa = Ser, Glu or Gln
<220> FEATURE:
<221> NAME/KEY: MOD_RES
<222> LOCATION: (296)..(296)
<223> OTHER INFORMATION: Xaa = His, Tyr or Leu
<220> FEATURE:
<221> NAME/KEY: MOD_RES
<222> LOCATION: (297)..(297)
<223> OTHER INFORMATION: Xaa = Ala, Lys or Asp
<220> FEATURE:
<221> NAME/KEY: MOD_RES
<222> LOCATION: (298)..(298)
<223> OTHER INFORMATION: Xaa = Lys or Leu
<220> FEATURE:
<221> NAME/KEY: MOD_RES
<222> LOCATION: (300)..(300)
<223> OTHER INFORMATION: Xaa = Thr or Glu

<400> SEQUENCE: 22

Met Leu Arg Leu Lys Thr Gln Asp Ser Arg Leu Lys Thr Gln Asp Ser
1               5                   10                  15

Arg Leu Lys Thr Gln Asp Ser Arg Leu Lys Thr Gln Asp Ser Arg Leu
            20                  25                  30

Lys Thr Gln Asp Ser Arg Leu Lys Xaa Gln Xaa Xaa Xaa Leu Lys Thr
        35                  40                  45

Xaa Xaa Xaa Xaa Leu Xaa Xaa Xaa Xaa Xaa Xaa Xaa Xaa Xaa Xaa Xaa
50                  55                  60

Thr Xaa Leu Xaa Asn Xaa Xaa Xaa Phe Ser Val Xaa Xaa Asn Xaa Xaa
65                  70                  75                  80

Phe Xaa Asn Xaa Xaa Xaa Xaa Gly Asn Xaa Xaa Xaa Ser Xaa Xaa Xaa
                85                  90                  95

Xaa Ile Xaa Xaa Xaa Gly Asn Asn Xaa Xaa Leu Xaa Ile Xaa Asp Asp
            100                 105                 110

Val Glu Xaa Xaa Xaa Leu Xaa Xaa Ser Phe Xaa Xaa Asp Xaa Asn Tyr
        115                 120                 125

Val Arg Ile His Lys Asn Ser Lys Ile Lys Gly Asp Ile Val Ala Xaa
130                 135                 140

Xaa Gly Ser Xaa Xaa Xaa Ile Xaa Xaa Xaa Thr Thr Met Gly Asn Gly
145                 150                 155                 160

Xaa Xaa Xaa Ile Xaa Xaa Lys Xaa Xaa Xaa Ser Ile Gly Xaa Asp Cys
                165                 170                 175

Met Xaa Ala Xaa Xaa Xaa Xaa Arg Xaa Xaa Asp Xaa His Pro Ile
            180                 185                 190

Phe Xaa Ile Xaa Asn Xaa Xaa Arg Ile Asn Xaa Xaa Lys Asp Xaa Ile
        195                 200                 205

Ile Xaa Xaa Xaa Val Trp Xaa Gly Arg Asn Val Xaa Ile Xaa Lys Gly
```

```
                    210                 215                 220
Val Xaa Gly Xaa Gly Xaa Val Ile Gly Xaa Xaa Xaa Val Val Thr
225                 230                 235                 240

Lys Asp Val Pro Glu Pro Xaa Cys Xaa Xaa Ala Gly Xaa Pro Ala Lys
                    245                 250                 255

Ile Ile Lys Xaa Arg Phe Asn Glu Lys Thr Ile Glu Arg Leu Leu Asn
                260                 265                 270

Ile Xaa Trp Xaa Arg Xaa Xaa Xaa Ala Xaa Xaa Xaa Xaa Asp Asp Xaa
            275                 280                 285

Asn Leu Xaa Xaa Asn Xaa Tyr Xaa Xaa Xaa Leu Xaa Gln Lys Ile Ile
        290                 295                 300

Lys Lys Ser Ile Ser Tyr Tyr Asn Pro Asn Lys Leu Tyr Phe Arg Asp
305                 310                 315                 320

Ile Leu Glu Leu Lys Ser Lys Lys Ile Phe Asn Leu Phe
                325                 330

<210> SEQ ID NO 23
<211> LENGTH: 286
<212> TYPE: PRT
<213> ORGANISM: Escherichia coli
<220> FEATURE:
<221> NAME/KEY: MISC_FEATURE
<223> OTHER INFORMATION: E. coli strain RS164 serotype K1 NeuO
      polysialic acid O-acetyltransferase

<400> SEQUENCE: 23

Met Leu Arg Leu Lys Thr Gln Asp Ser Arg Leu Lys Thr Gln Asp Ser
1               5                   10                  15

Arg Leu Lys Thr Gln Asp Ser Arg Leu Lys Thr Gln Asp Ser Arg Leu
                20                  25                  30

Lys Thr Gln Asp Ser Arg Leu Lys Thr Gln Asp Ser Arg Leu Lys Thr
            35                  40                  45

Gln Asp Ser Arg Leu Lys Thr Gln Asp Ser Arg Leu Lys Thr Gln Asp
        50                  55                  60

Ser Arg Leu Lys Thr Gln Asp Ser Phe Ser Val Asp Asp Asn Gly Ser
65                  70                  75                  80

Gly Asn Val Phe Val Cys Gly Asp Leu Val Asn Ser Lys Glu Asn Lys
                85                  90                  95

Val Gln Phe Asn Gly Asn Asn Asn Lys Leu Ile Ile Glu Asp Asp Val
            100                 105                 110

Glu Cys Arg Trp Leu Thr Val Ile Phe Arg Gly Asp Asn Asn Tyr Val
        115                 120                 125

Arg Ile His Lys Asn Ser Lys Ile Lys Gly Asp Ile Val Ala Thr Lys
    130                 135                 140

Gly Ser Lys Val Ile Ile Gly Arg Arg Thr Thr Ile Gly Ala Gly Phe
145                 150                 155                 160

Glu Val Val Thr Asp Lys Cys Asn Val Thr Ile Gly His Asp Cys Met
                165                 170                 175

Ile Ala Arg Asp Val Ile Leu Arg Ala Ser Asp Gly His Pro Ile Phe
            180                 185                 190

Asp Ile His Ser Lys Lys Arg Ile Asn Trp Ala Lys Asp Ile Ile Ile
        195                 200                 205

Ser Ser Tyr Val Trp Val Gly Arg Asn Val Ser Ile Met Lys Gly Val
    210                 215                 220

Ser Val Gly Ser Gly Ser Val Ile Gly Tyr Gly Ser Ile Val Thr Lys
225                 230                 235                 240
```

```
Asp Val Pro Ser Met Cys Ala Ala Gly Asn Pro Ala Lys Ile Ile
            245                 250                 255

Lys Arg Asn Ile Ile Trp Ala Arg Thr Asp Lys Ala Glu Leu Ile Ser
        260                 265                 270

Asp Asp Lys Arg Cys Ser Ser Tyr His Ala Lys Leu Thr Gln
        275                 280                 285

<210> SEQ ID NO 24
<211> LENGTH: 215
<212> TYPE: PRT
<213> ORGANISM: Neisseria meningitidis
<220> FEATURE:
<221> NAME/KEY: MISC_FEATURE
<223> OTHER INFORMATION: N. meningitidis serogroup Y OatY ORF downstream
      from polysialyltransferase (pst) gene

<400> SEQUENCE: 24

Met Gly Thr His Met Tyr Ser Glu Gln Gly Ile Asn Asn Thr Ile Asn
1               5                   10                  15

Ile Ser Thr Thr Ser Leu Thr Asn Ala Thr Gln Leu Thr Val Ile Gly
            20                  25                  30

Asn Asn Asn Ser Val Tyr Ile Gly Asn Asn Cys Lys Ile Val Ser Ser
        35                  40                  45

Asn Ile Arg Leu Lys Gly Asn Asn Ile Thr Leu Phe Ile Ala Asp Asp
    50                  55                  60

Val Glu Asn Met Gly Leu Val Cys Ser Leu His Ser Asp Cys Ser Leu
65                  70                  75                  80

Gln Ile Gln Ala Lys Thr Thr Met Gly Asn Gly Glu Ile Thr Ile Ala
                85                  90                  95

Glu Lys Gly Lys Ile Ser Ile Gly Lys Asp Cys Met Leu Ala His Gly
            100                 105                 110

Tyr Glu Ile Arg Asn Thr Asp Met His Pro Ile Tyr Ser Leu Glu Asn
        115                 120                 125

Gly Glu Arg Ile Asn His Gly Lys Asp Val Ile Ile Gly Asn His Val
    130                 135                 140

Trp Leu Gly Arg Asn Val Thr Ile Leu Lys Gly Val Cys Ile Pro Asn
145                 150                 155                 160

Asn Val Val Gly Ser His Thr Val Leu Tyr Lys Ser Phe Lys Glu
                165                 170                 175

Pro Asn Cys Val Ile Ala Gly Ser Pro Ala Lys Ile Val Lys Glu Asn
            180                 185                 190

Ile Val Trp Gly Arg Lys Met Tyr His Ser Thr Met Tyr Asp Asp Pro
        195                 200                 205

Thr Leu Asn Glu Phe Tyr Lys
    210                 215

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:"FLAG tag",
      epitope tag for anti-FLAG monoclonal antibody

<400> SEQUENCE: 25

Asp Tyr Lys Asp Asp Asp Lys
1               5
```

```
<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence:purification
      or epitope tag DDDDK (EC5)

<400> SEQUENCE: 26

Asp Asp Asp Asp Lys
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence:6 residue
      peptide purification or epitope tag derived from Polyoma middle T
      protein

<400> SEQUENCE: 27

Glu Tyr Met Pro Met Glu
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence:
      hexahistidine peptide epitope tag, metal chelate affinity ligand,
      affinity tag

<400> SEQUENCE: 28

His His His His His His
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence:sialate-O-
      acetyltransferase (SOAT) sialate binding motif
<220> FEATURE:
<221> NAME/KEY: MOD_RES
<222> LOCATION: (3)..(3)
<223> OTHER INFORMATION: X aa= any amino acid

<400> SEQUENCE: 29

Ala Gly Xaa Pro Ala Lys Ile
1               5

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence:orf11 gene
      SOAT protein PCR amplification primer CJ-175 with NdeI site

<400> SEQUENCE: 30
cttaggaggt catatggaaa aataacctt aaaatgc                              37

<210> SEQ ID NO 31
<211> LENGTH: 44
<212> TYPE: DNA
<213> ORGANISM: Artificial Sequence
```

-continued

```
<220> FEATURE:
<223> OTHER INFORMATION: Description of Artificial Sequence:orf11 gene
      SOAT protein PCR amplification primer CJ-176 with SalI site

<400> SEQUENCE: 31
cctaggtcga cttaaaatag attaaaaatt tttttttgatt ttag                    44

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence:SOAT protein
      LOS locus PCR amplification primer CJ42 in heptosylTase-II

<400> SEQUENCE: 32
gccattaccg tatcgcctaa ccagg                                          25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence:SOAT protein
      LOS locus PCR amplification primer CJ43 in heptosylTase-I

<400> SEQUENCE: 33
aaagaatacg aatttgctaa agagg                                          25
```

SOAT POLYPEPTIDE REACTION MIXTURE

CROSS-REFERENCES TO RELATED APPLICATIONS

This application is a U.S. National Phase Application under 35 U.S.C. §371 of International Application No. PCT/CA2006/001320, filed on Aug. 11, 2006, which claims the benefit of U.S. Provisional Application No. 60/707,843, filed Aug. 11, 2005, which is herein incorporated by reference for all purposes.

FIELD OF INVENTION

The invention relates to sialate-O-acetyltransferase (SOAT) polypeptides, nucleic acids that encode the polypeptides, and methods of using the polypeptides.

BACKGROUND OF THE INVENTION

As the terminal residue of membrane-associated glycoconjugates in vertebrates and higher invertebrates, sialic acids are important parts of the cellular apparatus devoted to the detection and integration of environmental stimuli. Several pathogenic microorganisms are known to incorporate sialic acids into their surface structures, thereby mimicking an abundant molecular component displayed by host cells, and providing a mechanism to evade immune response (Vimr, E. & Lichtensteiger, C., *Trends Microbiol.*, 10, 254-257 (2002)).

Sialic acids are a family of carboxylated monosaccharides that possess a common backbone structure of 9 carbon atoms. The structural diversity in the family arises as a result of various modifications to the biochemical precursor, and most naturally abundant member, 5-N-acetyl-neuraminic acid (NeuAc) (Schauer, R., *Glycobiology*. 1, 449-452 (1991); Varki, A., *Glycobiology*, 2, 25-40 (1992)). One commonly observed modification is O-acetylation at one or more of the hydroxyl groups at positions 4, 7, 8 or 9. This process, which is catalyzed enzymatically by sialate-O-acetyltransferases (SOATs), changes the binding and recognition characteristics of the underlying molecule, and as a result, diversifies the interaction potential for a given sialoglycan.

O-acetylation of sialic acids has been implicated in a growing number of physiological and pathological processes. In developing animals, ganglioside O-acetylation is associated with tissue growth and differentiation (Constantine-Paton, M. et al., *Nature*, 324, 459-462 (1986); Shi, W. X. et al. *J. Biol. Chem.*, 271, 31517-31525. (1996)). This process is of clinical importance because different modification patterns have been observed in human cell lines that have undergone malignant transformation (Cheresh, D. A. et al., *Science*, 225, 844-846. (1984); Hutchins, J. T. et al. *Cancer Res.*, 48, 483-489 (1988)). Therefore O-acetylated gangliosides could serve as targets for directed cancer therapies. O-acetylation has contrasting effects on the process of viral attachment to membrane-bound sialoglycans; this is an obligatory modification for the association of some enteric and respiratory viruses, but inhibits binding by others (Herrler, G. et al. *EMBO J.*, 4, 1503-1506 (1985); Smits, S. L. et al., *J. Biol. Chem.*, 280, 6933-6941 (2005)). As a final example, the sialylated polysaccharide capsules of group B *Streptococcus* (Lewis, A. L. et al., *Proc. Natl. Acad. Sci. USA*, 101, 11123-11128 (2004)), *Escherichia coli* K1 (11) (Orskov, F. et al., *J. Exp. Med.*, 149, 669-685 (1979)) and *Neisseria meningitidis* serogroup C, W-135 and Y (Bhattacharjee, A. et al., *Can. J. Biochem.*, 54, 1-8 (1976)) have been shown to be O-acetylated in some cases, which results in altered immunogenic properties.

The mucosal pathogen *Campylobacter jejuni* is a leading cause of diarrheal disease and of food-borne gastroenteritis worldwide (Nachamkin, I. et al., *Clin. Microbiol.*, Rev. 11, 555-567 (1998)). This organism exhibits a highly variable array of cell-surface glycans that are associated with virulence (Gilbert, M. et al., *J. Biol. Chem.*, 277, 327-337 (2002); Szymanski, C. M. et al., *J. Biol. Chem.*, 278, 24509-24520 (2003)). In several strains of *C. jejuni*, the glycan component of the lipo-oligosaccharide (LOS) is sialylated, and structurally similar to gangliosides (Aspinall, G. O. et al., *Eur. J. Biochem.*, 213, 1017-1027 (1993); Aspinall, G. O. et al., *Eur. J. Biochem.*, 213, 1029-1037 (1993); Aspinall, G. O. et al., *Biochemistry* 33, 241-249 (1994); St Michael, F. et al., *Eur. J. Biochem.*, 269, 5119-5136 (2002)). There is an accumulating body of evidence to suggest that the LOS from these strains may be responsible for generating antibodies that are cross-reactive with host epitopes found in abundance in nervous tissue, triggering an auto-immune response, which gives rise to Guillain-Barré syndrome (Godschalk, P. C. et al., *J. Clin. Invest.*, 114, 1659-1665 (2004); Yuki, N. et al., *Proc. Natl. Acad. Sci. USA*, 101, 11404-11409 (2004)).

As yet, there is no conclusive biochemical data to confirm the presence of O-acetylated NeuAc in the LOS of *C. jejuni* strains. This, we believe, is a result of the unique challenge inherent in the characterization of the glycan component of LOS; conventional spectroscopic techniques require the prior removal of the fatty acyl components. Unfortunately, chemical treatments used to accomplish this task have the undesired consequence of cleaving NeuAc residues, and/or saponification of O-acetyl modifications. NeuAc has been found to be incorporated into the LOS of *Haemophilus influenzae* (Hood, D. W. et al., *Mol. Microbiol.*, 33, 679-692 (1999)), *Neisseria* spp. (Smith, H., *Microb. Pathog.*, 19, 365-377 (1995)), and *C. jejuni* (Aspinall, G. O. et al., *Biochemistry*, 33, 241-249 (1994)), however, there have been no reports of O-acetylated species. Without evidence of the O-acetylated species, there has been a related failure to identify bacterial enzymes that synthesize such compounds. The present invention meets this and other needs.

BRIEF SUMMARY OF THE INVENTION

The present invention provides sialate-O-acetyltransferase (SOAT) polypeptides, nucleic acids that encode the polypeptides and methods of using the SOAT polypeptides to acetylate oligosaccharides. In one aspect, the invention also provides reaction mixtures that include SOAT polypeptides that transfer an acetyl moiety from a donor substrate to an acceptor substrate. Such a reaction mixture includes, e.g., the SOAT polypeptide, the substrates of the enzyme, i.e., a donor substrate and an acceptor substrate. The SOAT polypeptide can be present in the reaction mixtures as e.g., a purified or partially purified SOAT protein, a host cell that expresses a recombinant SOAT protein, or a permeabilized host cell that expressed a recombinant SOAT protein. In preferred embodiments, the reaction mixtures include, e.g., a purified or partially purified SOAT protein, or a permeabilized host cell that expressed a recombinant SOAT protein.

In some embodiments, the reaction mixtures include a recombinant SOAT polypeptide, with an amino acid sequence that has at least 80% identity to SEQ ID NO:10 and that transfer an acetyl moiety from a donor substrate to an acceptor substrate. In one embodiment, the SOAT polypeptide has at least 90% identity to SEQ ID NO:10. In another embodiment, the SOAT polypeptide comprises an amino acid sequence with at least 95% identity to SEQ ID NO:10. In a further embodiment, the SOAT polypeptide comprises an amino acid sequence selected from the SEQ ID NO:8, SEQ ID NO:10, SEQ ID NO:12, and SEQ ID NO:14. In one preferred embodiment, the SOAT polypeptide comprises the amino acid sequence of SEQ ID NO:10.

In one embodiment, the reaction mixture includes an acceptor substrate that is an oligosaccharide that includes a sialic acid moiety with a 2,8 linkage to another sugar. In another embodiment, the acceptor substrate is an oligosaccharide that includes a sialic acid moiety with a 2,3 linkage. In a further embodiment, the SOAT polypeptide adds an acetyl group to a sialic acid molecule at the 9 position.

In another aspect, the invention provides a method of making an oligosaccharide that includes an acetylated sialic acid moiety, by contacting a sialylated oligosaccharide with a donor substrate including an acetyl moiety and a recombinant SOAT polypeptide and then allowing transfer of the acetyl moiety to the sialylated oligosaccharide to occur, thereby producing the oligosaccharide that comprises an acetylated sialic acid moiety. In some embodiments, the recombinant SOAT polypeptide, has an amino acid sequence with at least 80% identity to SEQ ID NO:10. In one embodiment, the SOAT polypeptide has at least 90% identity to SEQ ID NO:10. In another embodiment, the SOAT polypeptide comprises an amino acid sequence with at least 95% identity to SEQ ID NO:10. In a further embodiment, the SOAT polypeptide comprises an amino acid sequence selected from the SEQ ID NO:8, SEQ ID NO:10, SEQ ID NO:12, and SEQ ID NO:14. In one preferred embodiment, the SOAT polypeptide comprises the amino acid sequence of SEQ ID NO:10.

In one embodiment, the method of acetylating an oligosaccharide is performed in vitro, e.g., using purified or partially purified SOAT polypeptides. In another embodiment, the method is performed in a host cell. The host cell can be permeabilized, or the host cell can be used for fermentative production of an acetylated oligosaccharide, e.g., using substrates or precursors of substrates that are taken up from the growth medium.

In a further embodiment, the method of acetylating an oligosaccharide is performed on a commercial scale.

In another aspect, the invention provides a recombinant sialate-O-acetyltransferase (SOAT) polypeptide, that comprises an amino acid sequence with at least 99% identity to SEQ ID NO:10 and that transfers an acetyl moiety from a donor substrate to an acceptor substrate. In one embodiment, the SOAT polypeptide comprises the amino acid sequence of SEQ ID NO:10. In a further embodiment, the SOAT polypeptide comprises a purification tag. In another aspect the invention provides a SOAT nucleic acid, that encodes the SOAT polypeptide. In one embodiment, the SOAT nucleic acid comprises a nucleic acid sequence of SEQ ID NO:9.

In a further aspect, the invention provides an expression vector that includes the recombinant SOAT nucleic acid that encodes an SOAT polypeptide. In some embodiments, the recombinant SOAT polypeptide, has an amino acid sequence with at least 80% identity to SEQ ID NO:10. In one embodiment, the SOAT polypeptide has at least 90% identity to SEQ ID NO:10. In another embodiment, the SOAT polypeptide comprises an amino acid sequence with at least 95% identity to SEQ ID NO:10. In a further embodiment, the SOAT polypeptide comprises an amino acid sequence selected from the SEQ ID NO:8, SEQ ID NO:10, SEQ ID NO:12, and SEQ ID NO:14. In one preferred embodiment, the SOAT polypeptide comprises the amino acid sequence of SEQ ID NO:10. The invention also encompasses host cells that include the expression vector, and methods of making SOAT polypeptides, by growing the host cells, under conditions suitable for expression of the SOAT polypeptide.

BRIEF DESCRIPTION OF THE DRAWINGS

FIGS. 2A and 2B provides a sequence alignment of Orf11 from various *C. jejuni* strains using ClustalW. The alignments are based on the orf11 translation products in various class A and B LOS strains. Only variable residues are shown in addition to the consensus sequence. The "*" indicate conserved residues, the ":" indicate strongly similar residues and the "." weakly similar residues. The *C. jejuni* strain numbers are indicated to the left of the sequences. The GenBank accession numbers are: AF215659 for ATCC 43432, AF400048 for ATCC 43438, AF167344 for ATCC 43446, AF401529 for ATCC 43449, AF401528 for ATCC 43456, AF130984 for OH4384. Prim. cons. is SEQ ID NO:19; 43449 is SEQ ID NO:14; 43456 is SEQ ID NO:15; 43438 is SEQ ID NO:10; 43432 is SEQ ID NO:8; 43446 is SEQ ID NO:12; OH4382 is SEQ ID NO:4; 4384 is SEQ ID NO:4.

FIG. 4 provides an alignment between the SOAT of *C. jejuni* strain ATCC 43438, i.e., SEQ ID NO: 10, a representative SOAT of the invention, and a single family domain from the Conserved Domain Database. Marchler-Bauer et al., *Nucleic Acids Res.* 33: D192-6 (2005). The alignment is between amino acid residues 78-216 of SEQ ID NO:10 (Query: SEQ ID NO: 20) and residues 59-190 (Subject: SEQ ID NO: 21) of the WbbJ, Acetyltransferase (isoleucine patch superfamily) domain, gnl|CDD|9985 COG0110. Identical residues are in bold and conserved residues are underlined.

FIGS. 5A and 5B, provides an alignment between the SOAT of *C. jejuni* strain ATCC 43438, i.e., SEQ ID NO:10, a representative SOAT of the invention, and some bacterial sialate-O-acetyltransferases. As in FIG. 2, a consensus sequence is shown [SEQ ID NO:22], and the "*" indicate conserved residues, the ":" indicate strongly similar residues and the "." weakly similar residues. The conserved sialate binding domain is indicated by underlining in the consensus sequence. Accession numbers are as follows: AY779018 for NeuO, Y13969 for OatY, and AF400048 for ATCC 43438.

DETAILED DESCRIPTION OF THE INVENTION

I. Introduction

Figure 1:
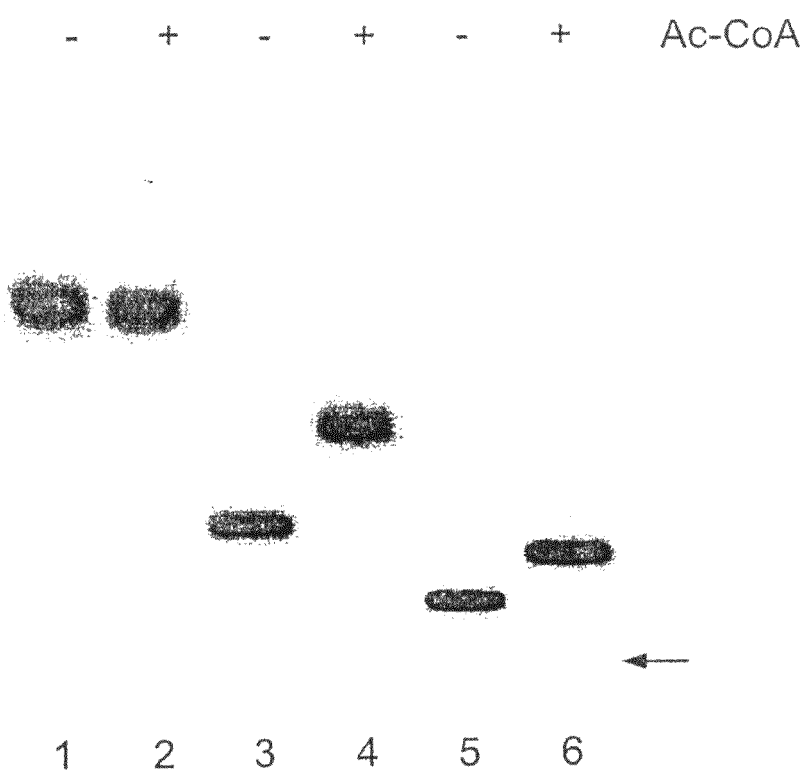
FIG. 1 demonstrates that the SOAT from *C. jejuni* ATCC 43446 (MalE-Orf11$^{43446}$) O-acetylates terminally α2,8-linked NeuAc and terminally α2,3-linked NeuAc. The acceptor specificity of the enzyme was assayed by monitoring the migration rate of FCHASE glycosides on a TLC plate following incubation in the absence (lanes 1, 3 and 5) and presence (lanes 2, 4 and 6) of acetyl-CoA. The acceptor possessing terminal α2,3-linked NeuAc, NeuAcα-2,3-Gal-β-1,4-Glc-FCHASE (lanes 1 and 2), shows lower levels of O-acetylation (visible in lane 2 as a faster migrating band). Enhanced migration rates resulting from O-acetylation are observed for the two acceptors possessing terminal α2,8-linked NeuAc: NeuAcα-2,-8-NeuAcα-2,3-Gal-O-1,4-Glc-FCHASE (lanes 3 and 4) and (NeuAcα-2,-8)$_2$-NeuAcα-2,3-Gal-β-1,4-Glc-FCHASE (lanes 5 and 6). The arrow indicates the origin of migration. The image is shown with reversed gray scale levels.

The invention provides the identification of a SOAT nucleic acid (orf11) in the LOS biosynthesis locus of *C. jejuni*. The SOAT nucleic acid was cloned into an *E. coli* expression vector and stably expressed as a fusion construct. Identification of this gene is the first evidence to indicate that LOS-bound NeuAc may be O-acetylated in *C. jejuni*, or any other bacterial species. The expression of the enzyme in a heterologous source, and subsequent purification, enabled precise biochemical characterization, which had proven intractable for SOATs previously identified in other organisms to date.

II. Definitions

The following abbreviations are used herein:
Ara=arabinosyl;
Fru=fructosyl;
Fuc=fucosyl;
Gal=galactosyl;
GalNAc=N-acetylgalactosaminyl;
Glc=glucosyl;
GlcNAc=N-acetylglucosaminyl;
Man=mannosyl; and
NeuAc=sialyl (N-acetylneuraminyl).

The terms "sialate-O-acetyltransferase", "SOAT", or a nucleic acid encoding a "sialate-O-acetyltransferase", "SOAT", refer to nucleic acids and polypeptide polymorphic variants, alleles, mutants, and interspecies homologs that: (1) have an amino acid sequence that has at least 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by a SOAT nucleic acid (for a SOAT nucleic acid sequence, see, e.g., SEQ ID NO:7, SEQ ID NO:9, SEQ ID NO:11, or SEQ ID NO:13) or to an amino acid sequence of a SOAT protein (for a SOAT protein sequence, see, e.g., SEQ ID NO:8, SEQ ID NO:10, SEQ ID NO:12, and SEQ ID NO:14); (2) bind to antibodies, e.g., polyclonal antibodies, raised against an immunogen comprising an amino acid sequence of a SOAT protein, and conservatively modified variants thereof; (3) specifically hybridize under stringent hybridization conditions to a sense or anti-sense strand corresponding to a nucleic acid sequence encoding a SOAT protein, and conservatively modified variants thereof; (4) have a nucleic acid sequence that has at least 90%, preferably at least 91%, 92%, 93%, 94%, 95%, 96%, 97%, 98%, 99%, or higher nucleotide sequence identity, preferably over a region of at least about 25, 50, 100, 200, 500, 1000, or more nucleotides or a full length sequence, to a SOAT nucleic acid, e.g., SEQ ID NO:7, SEQ ID NO:9, SEQ ID NO:11, or SEQ ID NO:13, or a nucleic acid encoding the catalytic domain. Preferably the catalytic domain has at least 90%, preferably at least 91%, 92%, 93%, 94%, 95%, 96%, 97%, 98%, 99% amino acid identity to the SOAT full length or catalytic domain of SEQ ID NO:8, SEQ ID NO:10, SEQ ID NO:12, or SEQ ID NO:14. A SOAT polynucleotide or polypeptide sequence is typically from a bacteria including, but not limited to, *Campylobacter*, *Haemophilus*, and *Pasteurella*. The nucleic acids and proteins of the invention include both naturally occurring or recombinant molecules. A SOAT polypeptide typically has O-acetyltransferase activity. O-acetyltransferase assays can be performed according to methods known to those of skill in the art, using appropriate donor substrates and acceptor substrates, as described herein.

An "acceptor substrate" or an "acceptor saccharide" for a SOAT polypeptide, e.g., a polypeptide comprising SEQ ID NO:8, SEQ ID NO:10, SEQ ID NO:12, or SEQ ID NO:14, is an oligosaccharide moiety that can act as an acceptor for a particular SOAT polypeptide, e.g. an oligosaccharide that comprises a sialic acid residue. When the acceptor substrate is contacted with the corresponding SOAT polypeptide and a donor substrate, and other necessary reaction mixture components, and the reaction mixture is incubated for a sufficient period of time, the SOAT polypeptide transfers acetyl residues from the donor substrate to the acceptor substrate. The acceptor substrate can vary for different types of a particular SOAT polypeptide. Accordingly, the term "acceptor substrate" is taken in context with the particular SOAT polypeptide of interest for a particular application. Acceptor substrates for SOAT polypeptides, e.g., SEQ ID NO:8, SEQ ID NO:10, SEQ ID NO:12, or SEQ ID NO:14, are described herein. In a preferred embodiment, the sialic acid residue to be acetylated is joined to an oligosaccharide in an α2,8 linkage. However, sialic acid residues can also be linked in α2,6 or α2,3 linkages. In another preferred embodiment, the acetyl group is added to the sialic acid residue at the 9 position.

A "donor substrate" for a SOAT polypeptide is an activated acetyl group. Such molecules generally consist of an activated acetyl group, however, longer carbon chains can also be transferred by the enzyme including propionyl-, butyryl-, and palmitoyl-groups. Donor substrates generally have the formula acetyl-X-R where X is an alkyl, a hetero alkyl, O or S; and R is CoA, an alkyl, a portion of CoA or a phenyl group. For example, a preferred donor substrate for SOAT polypeptides is acetyl-CoA. Other donor substrates for SOAT polypeptides include, e.g., propionyl-CoA, butyryl-CoA, and palmitoyl-CoA.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

As used herein, an "acetylated product saccharide" refers an oligosaccharide, a polysaccharide, or a carbohydrate moiety, either unconjugated or conjugated to a glycolipid, glycopeptide, or a glycoprotein, e.g., a biomolecule, that includes an acetyl moiety transferred by an SOAT polypeptide. Any of the above galactose moieties can be used, e.g., galactose or GalNAc. In preferred embodiments an acetyl group is transferred by a SOAT polypeptide. As the SOAT polypeptides of the invention can transfer, e.g., propionyl-, butyryl-, and palmitoyl-groups, unless other wise specified an acetylated product saccharide includes propionlyated, butyrylated, and palmitoylated products that have been modified by an SOAT polypeptide.

In some embodiments a sialic acid moiety is added to an oligosaccharide to produce an acceptor substrate, e.g., through the action of a sialyltransferase. Sialyltransferases are known to those of skill in the art and can be either a eukaryotic or prokaryotic protein. Bacterial sialyltransferases include e.g., sialyltransferases from *Neisseria, Campylobacter*, and *Haemophilis* species. Exemplary sialyltransferases are found in U.S. Pat. No. 6,096,529, issued Aug. 1, 2000; U.S. Pat. No. 6,503,744, issued Jan. 1, 2003; in U.S. Pat. No. 6,689,604, issued Feb. 10, 2004; in U.S. Pat. No. 6,699,705, issued Mar. 2, 2004; and in U.S. Ser. No. 60/610,807, filed Sep. 17, 2004; each of which is herein incorporated by reference for all purposes. In one embodiment a bifunctional sialyltransferase polypeptide, e.g., a sialyltransferase that transfers sialic acid in both α2,3 and α2,8 linkages is used. Bifunctional sialyltransferase polypeptides, such as the CstII protein, are disclosed, e.g., in U.S. Pat. No. 6,503,744, issued Jan. 1, 2003 and in U.S. Pat. No. 6,699,705, issued Mar. 2, 2004; both of which are herein incorporated by reference for all purposes.

The term "sialic acid" or "sialic acid moiety" refers to any member of a family of nine-carbon carboxylated sugars. The most common member of the sialic acid family is N-acetylneuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. In a preferred embodiment, 9-substituted sialic acids are excluded from the group of sialic acid moieties that serve as substrates for the disclosed SOAT polypeptides. For review of the sialic acid family, see, e.g., Varki, Glycobiology 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

Much of the nomenclature and general laboratory procedures required in this application can be found in Sambrook, et al., *Molecular Cloning: A Laboratory Manual* (2nd Ed.), Vol. 1-3, Cold Spring Harbor Laboratory, Cold Spring Harbor, N.Y., 1989. The manual is hereinafter referred to as "Sambrook et al."

"Commercial scale" refers to gram scale production of an acetylated product saccharide in a single reaction. In preferred embodiments, commercial scale refers to production of greater than about 50, 75, 80, 90, 100, 125, 150, 175, or 200 grams of acetylated product saccharide.

As used herein, a "truncated SOAT polypeptide" or grammatical variants, refers to a SOAT polypeptide that has been manipulated to remove at least one amino acid residue, relative to a wild type SOAT polypeptide that occurs in nature, so long as the truncated SOAT polypeptide retains enzymatic activity.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

Those of skill recognize that many amino acids can be substituted for one another in a protein without affecting the function of the protein, i.e., a conservative substitution can be the basis of a conservatively modified variant of a protein such as the disclosed SOAT proteins. An incomplete list of conservative amino acid substitutions follows. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V), Alanine (A); 6) Phenylalanine (F), Tyrosine (Y), Tryptophan (W); 7) Serine (S), Threonine (T), Cysteine (C); and 8) Cysteine (C), Methionine (M) (see, e.g., Creighton, *Proteins* (1984)).

The cells and methods of the invention are useful for producing a acetylated product saccharide, generally by transferring a acetyl moiety from a donor substrate to an acceptor molecule. The cells and methods of the invention are also useful for producing a acetylated product saccharide comprising additional sugar residues, generally by transferring a additional monosaccharide or a sulfate groups from a donor substrate to an acceptor molecule. The addition generally takes place at the non-reducing end of an oligosaccharide, polysaccharide (e.g., heparin, carragenin, and the like) or a carbohydrate moiety on a glycolipid or glycoprotein, e.g., a biomolecule. Biomolecules as defined here include but are not limited to biologically significant molecules such as carbohydrates, oligosaccharides, peptides (e.g., glycopeptides), proteins (e.g., glycoproteins), and lipids (e.g., glycolipids, phospholipids, sphingolipids and gangliosides).

The recombinant fusion protein of the invention can be constructed and expressed as a fusion protein with a molecular "purification tag" at one end, which facilitates purification of the protein. Such tags can also be used for immobilization of a protein of interest during the acetylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence Asp-TyrLysAspAspAspAspLys [SEQ ID NO:25] or a substantially identical variant thereof. Other epitope tags that can be used in the invention include, e.g., myc tag, AU1, AU5, DDDDK (EC5) [SEQ ID NO:26], E tag, E2 tag, Glu-Glu, a 6 residue peptide, EYMPME [SEQ ID NO:27], derived from the Polyoma middle T protein, HA, HSV, IRS, KT3, S tag, S1 tag, T7 tag, V5 tag, VSV-G, β-galactosidase, Gal4, green fluorescent protein (GFP), luciferase, protein C, protein A, cellulose binding protein, GST (glutathione S-transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abcam Ltd.; and Novus Biologicals, Inc.

Other suitable tags are known to those of skill in the art, and include, for example, an affinity tag such as a hexahistidine peptide [SEQ ID NO:28] or other poly-histidine peptides which will bind to metal ions such as nickel or cobalt ions. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, E. coli thioredoxin domains (vectors and antibodies commercially available from e.g., Santa Cruz Biotechnology, Inc. and Alpha Dioagnostic International, Inc.), and the carboxy-terminal half of the SUMO protein (vectors and antibodies commercially available from e.g., Life Sensors, Inc.). Starch binding domains, such as a maltose binding domain from E. coli and SBD (starch binding domain) from an amylase of A. niger, are described in WO 99/15636, herein incorporated by reference. Affinity purification of a fusion protein comprising a starch binding domain using a betacyclodextrin (BCD)-derivatized resin is described in U.S. Ser. No. 60/468,374, filed May 5, 2003, herein incorporated by reference in its entirety.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. The terms "nucleic acid", "nucleic acid sequence", and "polynucleotide" are used interchangeably herein.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant nucleic acid" refers to a nucleic acid that was artificially constructed (e.g., formed by linking two naturally-occurring or synthetic nucleic acid fragments). This term also applies to nucleic acids that are produced by replication or transcription of a nucleic acid that was artificially constructed. A "recombinant polypeptide" is expressed by transcription of a recombinant nucleic acid (i.e., a nucleic acid that is not native to the cell or that has been modified from its naturally occurring form), followed by translation of the resulting transcript.

A "heterologous polynucleotide" or a "heterologous nucleic acid", as used herein, is one that originates from a source foreign to the particular host cell, or, if from the same source, is modified from its original form. Thus, a heterologous glycosyltransferase gene in a prokaryotic host cell includes a glycosyltransferase gene that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "catalytic domain" refers to a portion of an enzyme that is sufficient to catalyze an enzymatic reaction that is normally carried out by the enzyme. For example, a catalytic domain of a SOAT polypeptide will include a sufficient portion of the SOAT to transfer a acetyl moiety from a donor substrate to an acceptor saccharide. A catalytic domain can include an entire enzyme, a subsequence thereof, or can include additional amino acid sequences that are not attached to the enzyme or subsequence as found in nature.

The term "isolated" refers to material that is substantially or essentially free from components which interfere with the activity of an enzyme. For cells, saccharides, nucleic acids, and polypeptides of the invention, the term "isolated" refers to material that is substantially or essentially free from components which normally accompany the material as found in its native state. Typically, isolated saccharides, proteins or nucleic acids of the invention are at least about 50%, 55%, 60%, 65%, 70%, 75%, 80% or 85% pure, usually at least about 90%, 91%, 92%, 93%, 94%, 95%, 96%, 97%, 98%, or 99% pure as measured by band intensity on a silver stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For oligonucleotides, or other galactosylated products, purity can be determined using, e.g., thin layer chromatography, HPLC, or mass spectroscopy.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80% or 85%, most preferably at least 90%, 91%, 92%, 93%, 94%, 95%, 96%, 97%, 98%, or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M $Na^+$ ion, typically about 0.01 to 1.0 M $Na^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to" or "specifically immunoreactive with", when referring to an antibody refers to a binding reaction which is determinative of the presence of the protein or other antigen in the presence of a heterogeneous population of proteins, saccharides, and other biologics. Thus, under designated immunoassay conditions, the specified antibodies bind preferentially to a particular antigen and do not bind in a significant amount to other molecules present in the sample. Specific binding to an antigen under such conditions requires an antibody that is selected for its specificity for a particular antigen. A variety of immunoassay formats can be used to select antibodies specifically immunoreactive with a particular antigen. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. In a preferred embodiment, antibodies that specifically bind to a SOAT protein are produced. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. The present invention includes antibodies that specifically bind to the disclosed SOAT polypeptides or fragments thereof.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F (ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

In one embodiment, the antibody is conjugated to an "effector" moiety. The effector moiety can be any number of molecules, including labeling moieties such as radioactive labels or fluorescent labels for use in diagnostic assays.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to IgE protein, polymorphic variants, alleles, orthologs, and conservatively modified variants, or splice variants, or portions thereof, can be selected to obtain only those polyclonal antibodies that are specifically immunoreactive with IgE proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" is a composition detectable by spectroscopic, photochemical, biochemical, immunochemical, or chemical means. For example, useful labels include $^{32}P$, $^{125}I$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radiolabel into the peptide, and used to detect antibodies specifically reactive with the peptide).

The term "immunoassay" is an assay that uses an antibody to specifically bind an antigen. The immunoassay is characterized by the use of specific binding properties of a particular antibody to isolate, target, and/or quantify the antigen.

The term "carrier molecule" means an immunogenic molecule containing antigenic determinants recognized by T cells. A carrier molecule can be a protein or can be a lipid. A carrier protein is conjugated to a polypeptide to render the polypeptide immunogenic. Carrier proteins include keyhole limpet hemocyanin, horseshoe crab hemocyanin, and bovine serum albumin.

The term "adjuvant" means a substance that nonspecifically enhances the immune response to an antigen. Adjuvants include Freund's adjuvant, either complete or incomplete; Titermax gold adjuvant; alum; and bacterial LPS.

The term "contacting" is used herein interchangeably with the following: combined with, added to, mixed with, passed over, incubated with, flowed over, etc.

III. SOAT Polypeptides

The SOAT polypeptides of the inventions comprise an amino acid sequence that is related to a conserved protein domain, the WbbJ, Acetyltransferase (isoleucine patch superfamily)gnl|CDD|9985 COG0110. The isoleucine patch superfamily domain is a protein domain that was identified as such based on sequence comparisons of proteins from different species that are believed to be orthologs. The isoleucine patch superfamily domain is a member of the Clusters of Ortholgous Groups (COG) database. See, e.g., Tatusov et al., BMC Bioinformatics 4:41 (2003). An alignment of amino acid residues 78-216 of SOAT with the sequence of the COG0110 sequence is provided in FIG. 4. The isoleucine patch superfamily domain appears to be found in acetyltransferases and to date 111 proteins with isoleucine patch superfamily domains are known. See, e.g., www.ncbi.nlm.nih.gov/COG/new/release/cow.cgi?cog=COG0110. However, the presence of the domain provides a general function prediction only. For example, the domain is shared by acetyltransferase proteins that acetylate a variety of substrates, including antibiotics and amino acids.

Computer programs that compare previously unknown sequences such as the disclosed SOAT amino acid sequences to known sequences, such as the isoleucine patch superfamily domain or other COGs, are freely available to those of skill. One such program is Cn3D which can be downloaded from www.ncbi.nlm.nih.gov/Structure/CN3D/cn3d.shtml. Cn3D correlates structure and sequence information: for example, a scientist can quickly find the residues in a crystal structure that correspond to known disease mutations, or conserved active site residues from a family of sequence homologs. Cn3D displays structure-structure alignments along with their structure-based sequence alignments, to emphasize what regions of a group of related proteins are most conserved in structure and sequence. Thus, using a program such as Cn3D, those of skill can identify conserved residues in the isoleucine patch superfamily domain of a SOAT polypeptide and moreover, can predict changes in amino acid residues that would likely not effect activity of the protein. In addition, using the Cn3D program, those of skill could also predict changes in amino acid residues that would be detrimental to SOAT activity and avoid them. Examples of such detrimental amino acid modifications are found e.g., in Table 1. Amino acid modifications can be selected from well known conservative amino acid substitutions, preferably of non-conserved or conserved amino acid residues Amino acid modifications can also be selected from corresponding amino acids in functionally similar proteins, see, e.g., FIGS. 2, 4, and 5.

Typically, the SOAT polypeptide will include a AG/"X"/PAKI [SEQ ID NO:29] motif (X is any residue), e.g., a sialate binding motif. Such motifs are disclosed in FIG. 5, which shows an alignment between Orf11 from ATCC 43438 and bacterial sialate-O-acetyltransferase polypeptides. In ORF11 of ATCC 43438 residues 194-200 are the AG/"X"/PAKI [SEQ ID NO:29] motif.

In some embodiments, the ORF11 SOAT polypeptides carry out the transfer of an O-acetyl group (or other group) directly to C9 of a sialic acid moiety. This is the first demonstration of the direct transfer of an O-acetyl group (or other group) directly to C9 of a sialic acid moiety by a bacterial enzyme. Moreover, previously, there was no conclusive biochemical evidence to demonstrate the presence of O-acetylated NeuAc in the LOS of C. jejuni strains. This is because of the particular composition of the glycan component of C. jejuni LOS; conventional spectroscopic techniques require the prior removal of the fatty acyl components. Unfortunately, chemical treatments used to perform this task cleave NeuAc residues, and/or saponificate O-acetyl modifications. The other bacterial sialate-O-acetyltransferase polypeptides in the alignment came from bacteria known to have acetylated sialic acid in capsule components. Those other bacterial sialate-O-acetyltransferase polypeptides have demonstrated sialate-O-acetyltransferase activity, but carry out different reactions than that of ORF11 polypeptides. NeuO (GenBank AY779018) is from *Escherichi coli* with K1 capsule. Poly-α-2,8-NeuAc capsule is acetylated at C7 and C9. Thus, NeuO is believed to acetylate at a specific position, followed by partial non-enzymatic migration to the other position. OatY (GenBank Y13969) is from *Neisseria meningitidis* with group Y capsule. In *Neisseria*, the capsule structure is a polymer of α-2,6-linked NeuAc to glucose. The NeuAc is acetylated at C7 and C9, likely by acetylation at a specific position, followed by partial non-enzymatic migration to the other position.

IV. Isolation of Nucleic Acids Encoding SOAT Polypeptides

Nucleic acids that encode SOAT polypeptides include nucleic acids that encode the SOAT polypeptides described above, i.e., SEQ ID NO:8, SEQ ID NO:10, SEQ ID NO:12, and SEQ ID NO:14, and conservatively modified variants of that sequence. The SOAT polypeptides of the invention catalyze the transfer of an acetyl moiety from a donor substrate to an acceptor substrate.

Nucleic acids that encode additional SOAT polypeptides based on the information disclosed herein, and methods of obtaining such nucleic acids, are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

A DNA that encodes a SOAT polypeptide, or a subsequences thereof, can be prepared by any suitable method described above, including, for example, cloning and restriction of appropriate sequences with restriction enzymes. In one preferred embodiment, nucleic acids encoding SOAT polypeptides are isolated by routine cloning methods. A nucleotide sequence of a SOAT polypeptide as provided in, for example, SEQ ID NO:7, SEQ ID NO:9, SEQ ID NO:11, or SEQ ID NO:13, can be used to provide probes that specifically hybridize to a gene encoding a SOAT polypeptide in a genomic DNA sample; or to an mRNA, encoding a SOAT polypeptide comprising, in a total RNA sample (e.g., in a Southern or Northern blot). Once the target nucleic acid encoding a SOAT polypeptide is identified, it can be isolated according to standard methods known to those of skill in the art (see, e.g., Sambrook et al. (1989) *Molecular Cloning: A Laboratory Manual, 2nd Ed., Vols.* 1-3, Cold Spring Harbor Laboratory; Berger and Kimmel (1987) *Methods in Enzymology, Vol.* 152: *Guide to Molecular Cloning Techniques*, San Diego: Academic Press, Inc.; or Ausubel et al. (1987) *Current Protocols in Molecular Biology*, Greene Publishing and Wiley-Interscience, New York). Further, the isolated nucleic acids can be cleaved with restriction enzymes to create nucleic acids encoding the full-length SOAT polypeptide, or subsequences thereof, e.g., containing subsequences encoding at least a subsequence of a catalytic domain of a SOAT polypeptide. These restriction enzyme fragments, encoding polypeptide or subsequences thereof, may then be ligated, for example, to produce a nucleic acid encoding SOAT protein.

A nucleic acid encoding a SOAT polypeptide, or a subsequence thereof, can be characterized by assaying for the expressed product. Assays based on the detection of the physical, chemical, or immunological properties of the expressed protein can be used. For example, one can identify a cloned SOAT nucleic acid, by the ability of a protein encoded by the nucleic acid to catalyze the transfer of an acetyl moiety from a donor substrate to an acceptor substrate. In one method, capillary electrophoresis is employed to detect the reaction products. This highly sensitive assay involves using either saccharide or disaccharide aminophenyl derivatives which are labeled with fluorescein as described in Wakarchuk et al. (1996) *J. Biol. Chem.* 271 (45): 28271-276. To assay for activity, NeuAcα-2,-8-NeuAcα-2,3-Gal-β-1,4-Glc-FCHASE, NeuAcα-2,3-Gal-β-1,4-Glc-FCHASE, NeuAcα-2,6-Gal-β-1,4-Glc-FCHASE or other sialylated-FCHASE molecule, is used as a substrate. The reaction products of other glycosyltransferases can be detected using capillary electrophoresis, e.g., to assay for a *Neisseria* lgtC enzyme, either FCHASE-AP-Lac or FCHASE-AP-Gal can be used, whereas for the *Neisseria* lgtB enzyme an appropriate reagent is FCHASE-AP-GlcNAc (Wakarchuk, supra). To assay for α2,8-sialyltransferase, GM3-FCHASE is used as a substrate. See, e.g., U.S. Pat. No. 6,503,744, which is herein incorporated by reference. Other methods for detection of oligosaccharide reaction products include thin layer chromatography and GC/MS and are disclosed in U.S. Pat. No. 6,503,744, which is herein incorporated by reference.

Also, a nucleic acid encoding a SOAT polypeptide, or a subsequence thereof, can be chemically synthesized. Suitable methods include the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding SOAT polypeptides, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., SalI). This will produce a nucleic acid encoding the desired SOAT polypeptide or a subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in Gen- Bank or other sources. Appropriate restriction enzyme sites can also be added to the nucleic acid encoding the SOAT protein or a protein subsequence thereof by site-directed mutagenesis. The plasmid containing the SOAT protein-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Some nucleic acids encoding bacterial SOAT proteins can be amplified using PCR primers based on the sequence of SOAT nucleic acids disclosed herein. In preferred embodiments, amplification is carried out under stringent conditions. Examples of PCR primers that can be used to amplify nucleic acid that encode SOAT proteins include the following primer pairs:

```
primer with NdeI site: CJ-175:
                                       [SEQ ID NO: 30]
CTTAGGAGGTCATATGGAAAAAATAACCTTAAAATGC primer with SalI site: CJ-176:
                                       [SEQ ID NO: 31]
CCTAGGTCGACTTAAAATAGATTAAAAATTTTTTTTGATTTTAG.
```

In some bacteria, nucleic acids encoding SOAT protein can be isolated by amplifying a specific chromosomal locus, e.g., the LOS locus of *C. jejuni*, and then identifying a SOAT nucleic acid typically found at that locus (see, e.g., U.S. Pat. No. 6,503,744). Examples of PCR primers that can be used to amplify an LOS locus comprising nucleic acids encoding a SOAT protein including the following primer pairs:

```
CJ42: Primer in heptosylTase-II
                                       [SEQ ID NO: 32]
5' GC CAT TAC CGT ATC GCC TAA CCA GG 3' 25 mer CJ43: Primer in heptosylTase-I
                                       [SEQ ID NO: 33]
5' AAA GAA TAC GAA TTT GCT AAA GAG G 3' 25 mer
```

Other physical properties of a recombinant SOAT polypeptide expressed from a particular nucleic acid, can be compared to properties of known SOAT polypeptides to provide another method of identifying suitable sequences or domains of the SOAT polypeptide that are determinants of acceptor substrate specificity and/or catalytic activity. Alternatively, a putative SOAT polypeptide or recombinant SOAT polypeptide can be mutated, and its role as an acetyltransferase, or the role of particular sequences or domains established by detecting a variation in the structure of a carbohydrate normally produced by the unmutated, naturally-occurring, or control SOAT polypeptide. Those of skill will recognize that mutation or modification of SOAT polypeptides of the invention can be facilitated by molecular biology techniques to manipulate the nucleic acids encoding the SOAT polypeptides, e.g., PCR. In addition, mutation of proteins by manipulation of encoding nucleic acid sequences is commercially available, from e.g., Modular Genetics, Inc. of Woburn, Mass., and GENEART, North America of Toronto, Calif.

Functional domains of newly identified SOAT polypeptides can be identified by using standard methods for mutating or modifying the polypeptides and testing them for activities such as acceptor substrate activity and/or catalytic activity, as described herein.

In an exemplary approach to cloning nucleic acids encoding SOAT proteins, the known nucleic acid or amino acid sequences of cloned SOAT polypeptides are aligned and compared to determine the amount of sequence identity between various SOAT polypeptides. This information can be used to identify and select protein domains that confer or modulate SOAT activities, e.g., acceptor substrate activity and/or catalytic activity based on the amount of sequence identity between the SOAT proteins of interest. For example, domains having sequence identity between the SOAT proteins of interest, and that are associated with a known activity, can be used to construct SOAT proteins containing that domain, and having the activity associated with that domain (e.g., acceptor substrate specificity and/or catalytic activity).

V. Expression of SOAT Polypeptides in Host Cells

SOAT proteins of the invention can be expressed in a variety of host cells, including *E. coli*, other bacterial hosts, and yeast. The host cells are preferably microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans*, and *C. humicola*), *Pichia* (e.g., *P. farinosa* and *P. ohmeri*), *Torulopsis* (e.g., *T. candida, T sphaerica, T. xylinus, T. famata*, and *T. versatilis*), *Debaryomyces* (e.g., *D. subglobosus, D. cantarellii, D. globosus, D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia, Enterobacter, Azotobacter, Erwinia, Klebsielia, Bacillus, Pseudomonas, Proteus*, and *Salmonella*.

Once expressed in a host cell, the SOAT polypeptides can be used to produce acetylated products. For example, the SOAT polypeptides can be isolated using standard protein purification techniques and used in in vitro reactions described herein to make acetylated products. Partially purified SOAT polypeptides can also be used in in vitro reactions to make acetylated products as can the permeabilized host cells. The host cells can also be used in an in vivo system (e.g., fermentative production) to produce acetylated products.

Typically, the polynucleotide that encodes the SOAT polypeptides is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., Nature (1977) 198: 1056), the tryptophan (trp) promoter system (Goeddel et al., Nucleic Acids Res. (1980) δ: 4057), the tac promoter (DeBoer, et al., Proc. Natl. Acad. Sci. U.S.A. (1983) 80:21-25); and the lambda-derived $P_L$ promoter and N-gene ribosome binding site (Shimatake et al., Nature (1981) 292: 128). The particular promoter system is not critical to the invention, any available promoter that functions in prokaryotes can be used.

For expression of SOAT proteins in prokaryotic cells other than E. coli, a promoter that functions in the particular prokaryotic species is required. Such promoters can be obtained from genes that have been cloned from the species, or heterologous promoters can be used. For example, the hybrid trp-lac promoter functions in Bacillus in addition to E. coli.

A ribosome binding site (RBS) is conveniently included in the expression cassettes of the invention. An RBS in E. coli, for example, consists of a nucleotide sequence 3-9 nucleotides in length located 3-11 nucleotides upstream of the initiation codon (Shine and Dalgarno, Nature (1975) 254: 34; Steitz, In Biological regulation and development: Gene expression (ed. R. F. Goldberger), vol. 1, p. 349, 1979, Plenum Publishing, NY).

For expression of the SOAT proteins in yeast, convenient promoters include GAL1-10 (Johnson and Davies (1984) Mol. Cell. Biol. 4:1440-1448) ADH2 (Russell et al. (1983) J. Biol. Chem. 258:2674-2682), PHO5 (EMBO J. (1982) 6:675-680), and MFα (Herskowitz and Oshima (1982) in The Molecular Biology of the Yeast Saccharomyces (eds. Strathem, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., Gene 61:265-275 (1987). For filamentous fungi such as, for example, strains of the fungi Aspergillus (McKnight et al., U.S. Pat. No. 4,935,349), examples of useful promoters include those derived from Aspergillus nidulans glycolytic genes, such as the ADH3 promoter (McKnight et al., EMBO J. 4: 2093 2099 (1985)) and the tpiA promoter. An example of a suitable terminator is the ADH3 terminator (McKnight et al.).

Either constitutive or regulated promoters can be used in the present invention. Regulated promoters can be advantageous because the host cells can be grown to high densities before expression of the fusion proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For E. coli and other bacterial host cells, inducible promoters are known to those of skill in the art. These include, for example, the lac promoter, the bacteriophage lambda $P_L$ promoter, the hybrid trp-lac promoter (Amann et al. (1983) Gene 25: 167; de Boer et al. (1983) Proc. Nat'l. Acad. Sci. USA 80: 21), and the bacteriophage T7 promoter (Studier et al. (1986) J. Mol. Biol.; Tabor et al., (1985) Proc. Nat'l. Acad. Sci. USA 82: 1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promoter, which is described in PCT Patent Application Publ. No. WO98/20111, [0093] A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Pub. No. WO98/20111.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in Streptomyces or Bacillus is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., E. coli, or other cells in which the vector is replicated prior to being introduced into the host cell. A number of selectable markers are known to those of skill in the art and are described for instance in Sambrook et al., supra.

Construction of suitable vectors containing one or more of the above listed components employs standard ligation techniques as described in the references cited above. Isolated plasmids or DNA fragments are cleaved, tailored, and religated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See, e.g., Squires, et al., (1988), *J. Biol. Chem.* 263: 16297-16302.

The SOAT polypeptides can be expressed intracellularly, or can be secreted from the cell. Intracellular expression often results in high yields. If necessary, the amount of soluble, active fusion protein may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the SOAT polypeptides are secreted from the cell, either into the periplasm or into the extracellular medium, the DNA sequence is linked to a cleavable signal peptide sequence. The signal sequence directs translocation of the fusion protein through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670). In another embodiment, the SOAT proteins are fused to a subsequence of protein A or bovine serum albumin (BSA), for example, to facilitate purification, secretion, or stability.

The SOAT polypeptides of the invention can also be further linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-glycosyltransferase and/or accessory enzyme amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one recombinant protein may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller et al. *Biotechnology* 7:698-704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

VI. Purification of SOAT Polypeptides

The SOAT proteins of the present invention can be expressed as intracellular proteins or as proteins that are secreted from the cell, and can be used in this form, in the methods of the present invention. For example, a crude cellular extract containing the expressed intracellular or secreted SOAT polypeptide can used in the methods of the present invention.

Alternatively, the SOAT polypeptide can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol.* 182: *Guide to Protein Purification*., Academic Press, Inc. N.Y. (1990)). Substantially pure compositions of at least about 70, 75, 80, 85, 90% homogeneity are preferred, and 92, 95, 98 to 99% or more homogeneity are most preferred. The purified proteins may also be used, e.g., as immunogens for antibody production.

To facilitate purification of the SOAT polypeptides of the invention, the nucleic acids that encode the proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the SOAT polypeptide of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)). Other purification or epitope tags include, e.g., AU1, AU5, DDDDK (EC5), E tag, E2 tag, Glu-Glu, a 6 residue peptide, EYMPME, derived from the Polyoma middle T protein, HA, HSV, IRS, KT3, S tage, S1 tag, T7 tag, V5 tag, VSV-G, β-galactosidase, Gal4, green fluorescent protein (GFP), luciferase, protein C, protein A, cellulose binding protein, GST (glutathione S-transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abeam Ltd.; and Novus Biologicals, Inc.

Purification tags also include maltose binding domains and starch binding domains. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, E. coli thioredoxin domains (vectors and antibodies commercially available from e.g., Santa Cruz Biotechnology, Inc. and Alpha Diagnostic International, Inc.), and the carboxy-terminal half of the SUMO protein (vectors and antibodies commercially available from e.g., Life Sensors Inc.). Starch binding domains, such as a maltose binding domain from E. coli and SBD (starch binding domain) from an amylase of A. niger, are described in WO 99/15636, herein incorporated by reference. Affinity purification of a fusion protein comprising a starch binding domain using a betacyclodextrin (BCD)-derivatized resin is described in WO 2005/014779, published Feb. 17, 2005, herein incorporated by reference in its entirety. In some embodiments, a SOAT polypeptide comprises more than one purification or epitope tag.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the catalytic or functional domains of the SOAT polypeptide without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

VIII. Acceptor Substrates

Typically, acceptor substrates include oligosaccharides or glycoconjugates that comprise a sialic acid residue for addition of an acetyl group. Examples of suitable acceptors include a sialic acid that is linked to another sialic acid residue by an α2,8 linkage, or a sialic acid that is linked by an α2,3 or α2,6 linkage. Suitable acceptors, include, for example, gangliosides, and other acceptors known to those of skill in the art. In some embodiments, the acceptor residue is a portion of an oligosaccharide that is attached to a peptide, a protein, a lipid, or a proteoglycan, for example.

Suitable acceptor substrates used by the SOAT polypeptides and methods of the invention include, but are not limited to, polysaccharides and oligosaccharides. The SOAT polypeptides described herein can also be used in multienzyme systems to produce a desired product from a convenient starting material.

Suitable acceptor substrates used by the SOAT polypeptides and methods of the invention include, but are not limited to, proteins, lipids, gangliosides and other biological structures (e.g., whole cells) that can be modified by the methods of the invention. These acceptor substrates will typically comprise the polysaccharide or oligosaccharide molecules described above. Exemplary structures, which can be modified by the methods of the invention include any a of a number glycolipids, glycoproteins and carbohydrate structures on cells known to those skilled in the art.

The present invention provides SOAT polypeptides that are selected for their ability to produce acetylated oligosaccharides, glycoproteins and glycolipids having desired oligosaccharide moieties.

For synthesis of acetylated glycoproteins, one can readily identify suitable SOAT polypeptides by reacting various amounts of a SOAT polypeptide of interest (e.g., 0.01-100 mU/mg protein) with a glycoprotein (e.g., at 1-10 mg/ml) to which is linked an oligosaccharide that has a potential acceptor site for acetylation by the SOAT protein of interest. The abilities of the recombinant SOAT proteins of the present invention to add a sugar residue at the desired acceptor site are compared, and a SOAT polypeptide having the desired property (e.g., acceptor substrate specificity or catalytic activity) is selected.

In general, the efficacy of the enzymatic synthesis of oligosaccharides, glycoproteins, and glycolipids, having desired acetylated oligosaccharide moieties, can be enhanced through use of recombinantly produced SOAT polypeptides of the present invention. Recombinant techniques enable production of the recombinant SOAT polypeptides in the large amounts that are required for large-scale in vitro acetylation of oligosaccharides, glycoproteins and glycolipids.

In some embodiments, suitable oligosaccharides, glycoproteins, and glycolipids for use by the SOAT polypeptides and methods of the invention can be glycoproteins and glycolipids immobilized on a solid support during the acetylation reaction. The term "solid support" also encompasses semi-solid supports. Preferably, the target glycoprotein or glycolipid is reversibly immobilized so that the respective glycoprotein or glycolipid can be released after the acetylation reaction is completed. Many suitable matrices are known to those of skill in the art. Ion exchange, for example, can be employed to temporarily immobilize a glycoprotein or glycolipid on an appropriate resin while the acetylation reaction proceeds. A ligand that specifically binds to the glycoprotein or glycolipid of interest can also be used for affinity-based immobilization. For example, antibodies that specifically bind to a glycoprotein are suitable. Also, where the glycoprotein of interest is itself an antibody or contains a fragment thereof, one can use protein A or G as the affinity resin. Dyes and other molecules that specifically bind to a glycoprotein or glycolipid of interest are also suitable.

Preferably, when the acceptor saccharide is a truncated version of the full-length glycoprotein, it preferably includes the biologically active subsequence of the full-length glycoprotein. Exemplary biologically active subsequences include, but are not limited to, enzyme active sites, receptor binding sites, ligand binding sites, complementarity determining regions of antibodies, and antigenic regions of antigens.

IX. Production of Acetylated Products

SOAT polypeptides can be used to make acetylated products in in vitro reactions mixes comprising purified or partially purified SOAT polypeptides or permeabilized cells that express recombinant SOAT polypeptides, or by in vivo reactions, e.g., by fermentative growth of recombinant microorganisms that comprise nucleotides that encode SOAT polypeptides.

A. In Vitro Reactions

The SOAT polypeptides can be used to make acetylated products in in vitro reactions mixes. The in vitro reaction mixtures can include permeabilized microorganisms comprising the SOAT polypeptides, partially purified SOAT polypeptides, or purified SOAT polypeptides; as well as donor substrates, acceptor substrates, and appropriate reaction buffers. For in vitro reactions, the recombinant proteins, such as SOAT polypeptides, acceptor substrates, donor substrates and other reaction mixture ingredients are combined by admixture in an aqueous reaction medium. Appropriate glycosyltransferases, e.g., sialyltransferases can be used in combination with the SOAT polypeptides, depending on the desired acetylated product. The medium generally has a pH value of about 5 to about 8.5. The selection of a medium is based on the ability of the medium to maintain pH value at the desired level. Thus, in some embodiments, the medium is buffered to a pH value of about 6.5. If a buffer is not used, the pH of the medium should be maintained at about 5 to 8.5, depending upon the particular glycosyltransferase used. For SOAT polypeptides, the pH range is preferably maintained from about 6.0 to 8.0. For sialyltransferases, the range is preferably from about 5.5 to about 8.0.

Enzyme amounts or concentrations are expressed in activity units, which is a measure of the initial rate of catalysis. One activity unit catalyzes the formation of 1 μmol of product per minute at a given temperature (typically 37° C.) and pH value (typically 7.5). Thus, 10 units of an enzyme is a catalytic amount of that enzyme where 10 μmol of substrate are converted to 10 μmol of product in one minute at a temperature of 37° C. and a pH value of 7.5.

The reaction mixture may include divalent metal cations ($Mg^{2+}$, $Mn^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

The reaction mixture so formed is maintained for a period of time sufficient to obtain the desired high yield of desired acetylated product. For large-scale preparations, the reaction will often be allowed to proceed for between about 0.5-240 hours, and more typically between about 1-36 hours.

B. In Vivo Reactions

The SOAT polypeptides can be used to make acetylated products by in vivo reactions, e.g., fermentative growth of recombinant microorganisms comprising the SOAT polypeptides. Fermentative growth of recombinant microorganisms can occur in the presence of medium that includes an acceptor substrate or a precursor to an acceptor substrate, e.g., lactose, and a donor substrate or a precursor to a donor substrate, e.g., sialic acid or N-acetylglucosamine (GlcNAc). See, e.g., Priem et al., *Glycobiology* 12:235-240 (2002) and U.S. Ser. No. 60/610,704, filed Sep. 17, 2004, which is herein incorporated by reference for all purposes.

The microorganism takes up the acceptor substrate or the precursor to the acceptor substrate and the donor substrate or the precursor to a donor substrate and the addition of the donor substrate to the acceptor substrate takes place in the living cell. The microorganism can be altered to facilitate uptake of the acceptor substrate or its precursor, e.g., by expressing a sugar transport protein. For example, where a sialylated oligosaccharide comprising lactose is the acceptor saccharide, *E. coli* cells that express the LacY permease can be used. Other methods can be used to decrease breakdown of an acceptor saccharide or to increase production of a donor saccharide or a precursor of the donor saccharide. In some embodiments, production of sialylated products is enhanced by manipulation of the host microorganism. For example, in *E. coli*, break down of sialic acid can be minimized by using a host strain that is lacking CMP-sialate synthase (NanA-). (In *E. coli*, CMP-sialate synthase appears to be a catabolic enzyme.) Also in *E. coli*, when lactose is, for example, the acceptor saccharide or an intermediate in synthesizing the galactosylated product, lactose breakdown can be minimized by using host cells that are LacZ-.

C. Characterization of and Isolation of Acetylated Products

The production of acetylated products can be monitored by e.g., determining that production of the desired product has occurred or by determining that a substrate such as the acceptor substrate has been depleted. Those of skill will recognize that acetylated products such as acetylated oligosaccharide, can be identified using techniques such as chromatography, e.g., using paper or TLC plates, or by mass spectrometry, e.g., MALDI-TOF spectrometry, or by NMR spectroscopy. Methods of identification of acetylated products are known to those of skill in the art and are found, e.g., in U.S. Pat. No. 6,699, 705, which is herein incorporated by reference for all purposes and in Varki et al., *Preparation and Analysis of Glycoconjugates*, in Current Protocols in Molecular Biology, Chapter 17 (Ausubel et al. eds, 1993).

In some embodiments, the SOAT polypeptides and methods of the present invention are used to enzymatically synthesize an acetylated product that has a substantially uniform acetylation pattern. In the resulting products, at least about 30% of the potential acceptor sites of interest are acetylated. More preferably, at least about 50% of the potential acceptor substrates of interest are acetylated, and still more preferably to at least 70% of the potential acceptor substrates of interest are acetylated.

The term "altered" refers to the glycoprotein or glycolipid of interest having an acetylation pattern that, after application of the SOAT polypeptides and methods of the invention, is different from that observed on the glycoprotein as originally produced. An example of such acetylated glycoconjugates are glycoproteins in which the glycoforms of the glycoproteins are different from those found on the glycoprotein when it is produced by cells of the organism to which the glycoprotein is native. Also provided are SOAT polypeptides and methods of using such proteins for enzymatically synthesizing glycoproteins and glycolipids in which the acetylation pattern of these glycoconjugates are modified compared to the acetylation pattern of the glycoconjugates as originally produced by a host cell, which can be of the same or a different species than the cells from which the native glycoconjugates are produced.

One can assess differences in acetylation patterns not only by structural analysis of the glycoproteins and glycolipids, but also by comparison of one or more biological activities of the glycoconjugates. For example, a glycoprotein having an "altered glycoform" includes one that exhibits an improvement in one more biological activities of the glycoprotein after the acetylation reaction compared to the unmodified glycoprotein. For example, an altered glycoconjugate includes one that, after application of the SOAT polypeptides and methods of the invention, exhibits a greater binding affinity for a ligand or receptor of interest, a greater therapeutic half-life, reduced antigenicity, and targeting to specific tissues. The amount of improvement observed is preferably statistically significant, and is more preferably at least about a 25% improvement, and still more preferably is at least about 30%, 40%, 50%, 60%, 70%, and even still more preferably is at least 80%, 90%, or 95%.

The products produced using SOAT polypeptides can be used without purification. However, standard, well known techniques, for example, thin or thick layer chromatography, ion exchange chromatography, or membrane filtration can be used for recovery of acetylated products. Also, for example, membrane filtration, utilizing a nanofiltration or reverse osmotic membrane as described in commonly assigned AU Patent No. 735695 may be used. As a further example, membrane filtration wherein the membranes have a molecular weight cutoff of about 1000 to about 10,000 Daltons can be used to remove proteins. As another example, nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used. Thus, for example, the oligosaccharides produced by the compositions and methods of the present invention can be retained in the membrane and contaminating salts will pass through.

It must be noted that as used herein and in the appended claims, the singular forms "a", "and", and "the" include plural referents unless the context clearly dictates otherwise. Thus, for example, reference to "a nucleic acid" includes a plurality of such nucleic acids and reference to "the polypeptide" includes reference to one or more polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citations are incorporated herein by reference.

EXAMPLES

Example 1

Cloning the SOAT Nucleic Acid from *C. jejuni* Strains

Cloning of the SOAT from *C. jejuni*.

The orf11 gene was amplified from the various *C. jejuni* strains using the Pwo polymerase and the following primers: CJ-175 (5' CTTAGGAGGTCATATGGAAAAAATAAC-CTTAAAATGC 3' [SEQ ID NO:30] 137 mer, NdeI site in italics) and CJ-176 (5' CCTAGGTCGACTTAAAATAGAT-TAAAAATTTTTTTTGATTTTAG 3' [SEQ ID NO:31] 44 mer, SalI site in italics). The PCR products were digested with NdeI and SalI and cloned in pCWori+(-lacZ) containing the sequence encoding the *E. coli* maltose-binding protein (without the leader peptide) and the thrombin cleavage site.

Purification of the Recombinant SOAT.

*E. coli* AD202 containing construct CJL-130 (Orf11 from *C. jejuni* ATCC 43446 in pCWori+) was grown in 2 YT medium containing 150 µg/mL ampicillin and 2 g/L glucose. The culture was incubated at 37° C. until $A_{600}$=0.35, induced with 1 mM IPTG, and then incubated overnight at 20° C. The cells were broken using an Avestin C5 Emulsiflex cell disruptor (Avestin, Ottawa) and the MalE-Orf11 fusion was purified by affinity chromatography on amylose resin following the manufacturer's instructions (New England Biolabs, Beverly, Mass.).

In Vitro O-Acetyltransferase Reaction.

FCHASE-labeled oligosaccharides were prepared as described previously (Wakarchuk, W. W. & Cunningham, A. M., *Methods Mol. Biol.*, 213, 263-274 (2003)). The acetyltransferase activity was assayed using 0.5 mM of NeuAcα-2,-8-NeuAcα-2,3-Gal-β-1,4-Glc-FCHASE, 1 mM acetyl-CoA, 50 mM Mes, pH 6.5, 10 mM $MgCl_2$ and 1 mM DTT. The enzymatic reactions were performed at 37° C. for 5 min and were stopped by the addition of acetonitrile (25% final). The samples were analyzed by capillary electrophoresis (CE) as described previously (Wakarchuk, W. W. & Cunningham, A. M., *Methods Mol. Biol.*, 213, 263-274 (2003)). Quantitation of the reactions was performed by integration of the CE trace peaks using the MDQ 32 Karat software (Beckman, Calif.). TLC analysis was performed with aluminum backed silica plates that were developed in ethyl acetate:methanol: water:acetic acid (4:2:1:0.1).

Orf11 of *C. Jejuni* ATCC 43446 has Sialate-O-Acetyltransferase Activity.

Based on the gene complement in the LOS biosynthesis locus, *C. jejuni* strains can be grouped into eight classes (Parker, C. T. et al., *J. Clin. Microbiol.* 43:2771-2781 (2005)). Class A, B and C strains are capable of synthesizing sialylated oligosaccharide cores that mimic ganglioside structures (Gilbert, M. et al., *J. Biol. Chem.*, 277, 327-337 (2002)), and are thought to be those responsible for triggering the onset of Guillain-Barré syndrome in humans (Godschalk, P. C. et al., *J. Clin. Invest.*, 114, 1659-1665 (2004)). Strains belonging to classes A and B also possess a gene, originally named orf11, that encodes a protein showing homology with various acetyltransferases of the NodL-LacA-CysE family, although it was not possible to determine its acceptor based on the activity of the homologues. This gene is located immediately downstream of the four genes (cstII, neuB, neuC and neuA) involved in sialylation of the LOS outer core.

In the biosynthetic pathway of sialoglycans, free forms of sialic acid are CMP-activated prior to their transfer, by sialyltransferases, onto nascent oligosaccharides. In group B Streptococcus, sialic acids destined for the capsular polysaccharide are O-acetylated prior to activation (Lewis, A. L. et al., Proc. Natl. Acad. Sci. USA, 101, 11123-11128 (2004)), and in the Golgi apparatus of mammalian cells there is evidence that CMP-Sia may be the substrate for certain SOATs (Shen, Y. et al., Biol. Chem., 383, 307-317 (2002)).

Orf11 from C. jejuni ATCC 43446 was expressed as a MalE fusion construct (MalE-Orf11$^{43446}$) in E. coli and was purified by affinity chromatography. There was no evidence of O-acetylated product when purified MalE-Orf1143446 was incubated with either NeuAc or CMP-NeuAc as acceptor in the presence of acetyl-CoA (data not shown). We have used 6-(5-fluorescein-carboxamido)-hexanoic acid amide (FCHASE) glycosides as synthetic acceptors to confirm the biological role of several glycosyltransferases cloned from bacterial sources (Gilbert, M. et al., J. Biol. Chem., 275, 3896-3906 (2000); Gilbert, M. et al., J. Biol. Chem., 271, 28271-28276 (1996)). FCHASE derivatives were employed to establish that Orf11 from C. jejuni ATCC 43446 catalyses the transfer of the O-acetyl group to oligosaccharide-bound NeuAc, and that it has a strong preference for terminal α2,8-linked residues. Following incubation in the presence of acetyl-CoA, NeuAcα-2,8-NeuAcα-2,3-Gal-β-1,4-Glc-FCHASE and (NeuAcα-2,8)2-NeuAcα-2,3-Gal-β-1,4-Glc-FCHASE glycosides, possessing terminal α2,8-linked NeuAc, exhibited more rapid migration rates on a TLC plate as a result of O-acetylation (FIG. 1). The level of conversion to a higher mobility form was barely detectable when NeuAcα-2,3-Gal-O-1,4-Glc-FCHASE, possessing a terminal α2,3-linked NeuAc, was used as the acceptor (FIG. 1). The specific activity of the purified MalE-Orf11$^{43446}$ was 0.4 mU/mg with the mono-sialylated acceptor, 77.8 mU/mg with the di-sialylated acceptor and 17.2 mU/mg with the tri-sialylated acceptor. A recent study of a partially purified SOAT from guinea pig liver reported a similar ability to O-acetylate several compounds, at significantly diminished levels, that were not believed to be the natural substrates of the enzyme (Iwersen, M. et al., Biol. Chem., 384, 1035-1047 (2003)).

Sequence Variation of Orf11 in Various C. Jejuni Strains.

Sequences of orf11 proteins encoded by the LOS biosynthesis locus from 8 class A and B strains of C. jejuni are shown in FIG. 2. The orf11 gene from ATCC 43460 encodes a truncated protein (63 aa) because of a frame-shift mutation and is thus inactive. Since the translation products from C. jejuni OH4382 and OH4384 are identical, there are 6 distinct full-length Orf11 variants among the 8 class A and B loci that we sequenced. The level of protein sequence identity is high, with 94% of the residues being conserved among the 6 variants (FIG. 2). To assess how specific amino acid differences affected transferase activity, we cloned and expressed the 6 Orf11 variants as MalE fusion constructs. As described above, MalE-Orf11$^{43446}$ had high activity on terminal α-2,8-linked NeuAc and lower activity on α-2,3-linked NeuAc. MalE-Orf11$^{43438}$ and MalE-Orf11$^{43449}$ also had high activity on terminal α-2,8-linked NeuAc and lower activity on α-2,3-linked NeuAc. MalE-Orf11$^{43432}$ had low activity on α-2,8-linked NeuAc and no activity on α-2,3-linked NeuAc. MalE-Orf11$^{OH4382}$ and MalE-Orf11$^{43456}$ are both inactive. The results are summarized in Table 1. Single mutations are responsible for the inactivation of these variants since Orf11$^{OH4382}$ has only one amino acid difference (Asp75Gly) with Orf11$^{43449}$, as does MalE-Orf11$^{43456}$ (Glu91Gly) (Table 1 and FIG. 2).

TABLE 1

Variants of Orf11:

| C. jejuni strain | Penner type | Sequenced at NRC | GenBank # | Comments |
|---|---|---|---|---|
| OH4384 | HS:19 | Yes | AF130984 | Sequence ID No 24 in U.S. Pat. No. 6,503,744 B1 and Sequence ID No 38 in U.S. Pat. No. 6,699,705 B2 Inactive due to Gly75Asp mutation |
| OH4382 | HS:19 | Yes | None | Sequence is identical to OH4384 Inactive due to Gly75Asp mutation |
| ATCC 43432 | HS:4 | Yes | AF215659 | Low activity on terminal α-2,8-NeuAc |
| ATCC 43438 | HS:10 | Yes | AF400048 | High activity on terminal α-2,8-NeuAc and low activity on terminal α-2,3-NeuAc |
| ATCC 43446 | HS:19 | Yes | AF167344 | High activity on terminal α-2,8-NeuAc and low activity on terminal α-2,3-NeuAc |
| ATCC 43449 | HS:23 | Yes | AF401529 | High activity on terminal α-2,8-NeuAc and low activity on terminal α-2,3-NeuAc |
| ATCC 43456 | HS:36 | Yes | AF401528 | Inactive due to Gly91Glu mutation |
| ATCC 43460 | HS:41 | Yes | AY044868 | Truncated (63 aa), inactive |
| HB93-13 | HS:19 | No | AY297047 | Sequence is identical to HS:19 |

There is considerable sequence variation amongst proteins known to possess D-acetyltransferase activity. Some, however, exhibit sufficient homology to enable grouping into one of two families: the first, known as the NodL-LacA-CysE family, are water-soluble cytoplasmic proteins (Downie, J. A., Mol. Microbiol., 3, 1649-1651 (1989)), whereas the second, comprises a group of integral membrane proteins (Hara, O. & Hutchinson, C. R., J. Bacteriol., 174, 5141-5144 (1992)). As noted earlier, the enzyme we have identified in C. jejuni shows homology with the NodL-LacA-CysE family. Interestingly, a recently published sequence for a SOAT, which is involved in capsule production in Neisseria meningitides, also shows homology with the water-soluble family of O-acetyltransferases (Claus, H. et al., Mol. Microbiol., 51, 227-239 (2004)).

Example 2

Characterization of the SOAT Enzymatic Reaction

Determination of the O-acetylation site by NMR spectroscopy. Lyophilized O-acetyl-NeuAcα-2,-8-NeuAcα-2,3-Gal-β-1,4-Glc-FCHASE was dissolved in D$_2$O at a concentration of ~3 mM. Standard proton and carbon-correlated proton spectra were acquired, as described previously (Gilbert, M. et al., *J. Biol. Chem.*, 275, 3896-3906 (2000)), to assign the position of the O-acetyl group. The reported $^1$H chemical shifts are referenced with respect to the methyl group of acetone appearing at 2.225 ppm.

To address whether there was post-enzymatic migration of the O-acetyl group on the glycerol side chain, the acetylation of NeuAcα-2,-8-NeuAcα-2,3-Gal-β-1,4-Glc-FCHASE by the MalE-Orf11$^{43446}$ from *C. jejuni* was monitored in real-time by $^1$H-NMR. This was accomplished by recording successive $^1$H-1D spectra of the reaction over a period of 100 minutes at 37° C. The reaction mixture contained 2.5 mM NeuAcα-2,-8-NeuAcα-2,3-Gal-β-1,4-Glc-FCHASE, 5 mM acetyl-CoA, and 10 mM MgCl$_2$ in deuterated phosphate buffer (pH=6.5). The reaction was initiated upon addition of an aliquot of enzyme (8 mU). Roughly 5 min elapsed between the addition of the enzyme, and the acquisition of the first time-point (defined as t=0 min). Each spectrum took 2 minutes to acquire. The reaction progress was followed and quantified by integrating the O-acetyl and H9' resonances, which were both gave rise to well resolved peaks. The uncertainty associated with integration measurements is ~10%. All NMR data were acquired on Varian instruments operating at 500 and 600 MHz, and processed using the software Topspin (Bruker Biospin).

The SOAT from *C. Jejuni* HS:19 O-Acetylates at the 9-Position Directly.

Sialic acids have been found to be modified with O-acetyl groups at C4, and at any one of the three hydroxyl groups on the exocyclic side chain (i.e. C7, C8 and C9) (Schauer, R., *Glycobiology*. 1, 449-452 (1991); Varki, A., *Glycobiology*, 2, 25-40 (1992)). One of the peculiarities associated with O-acetylation to the exocyclic side chain is that this group will migrate spontaneously from the 7- to the 9-position, via the 8-O-acetyl species. 8-O-acetylated sialic acids are very unstable and exist only transiently, unless the hydroxyl group at C9 has already been modified, or is the linkage site. O-acetyl migration from the 7- to the 9-position, which has been observed directly in vitro using free forms of modified NeuAc in solution, occurs on a relatively slow time-scale under mild solution conditions ($t_{1/2}$≈10 h at pH 7, 37° C.), but is accelerated by raising the solution pH (Haverkamp, J. et al., *Eur. J. Biochem.*, 122, 305-311 (1982)). In almost all organisms where 9-O-acetylated sialoglycans have been detected, the de novo enzymatic product has been postulated to be the 7-O-acetylated species, which was converted to the 9-O-acetyl isomer following migration (Lewis, A. L. et al., *Proc. Natl. Acad. Sci. USA*, 101, 11123-11128 (2004); Shen, Y. et al., *Biol. Chem.*, 383, 307-317 (2002); Claus, H. et al., *Mol. Microbiol.*, 51, 227-239 (2004); Higa, H. H. et al., *J. Biol. Chem.*, 264, 19427-19434 (1989); Lemercinier, X. & Jones, C., *Carbohydr. Res.*, 296, 83-96 (1996); Vandamme-Feldhaus, V. & Schauer, R., *J. Biochem.* (*Tokyo*), 124, 111-121 (1998)). Varki and colleagues have demonstrated, however, that in the Golgi apparatus of mammalian systems, sialylated glycoconjugates are likely O-acetylated at both C7 and C9 directly, possibly by different SOATs (Diaz, S. et al., *J. Biol. Chem.*, 264, 19416-19426 (1989); Manzi, A. E. et al., *J. Biol. Chem.*, 265, 13091-13103 (1990)). The precise acceptor position has been difficult to determine in most instances due to the inability to purify these enzymes.

Using the SOAT from *C. jejuni* ATCC 43446 (MalE-Orf11$^{43446}$), we synthesized preparative quantities of 9-O-acetyl-NeuAcα-2,8-NeuAcα-2,3-Gal-β-1,4-Glc-FCHASE for analysis by NMR spectroscopy. We were able to assign the O-acetyl group to C9 position of the terminal NeuAc. This is demonstrated by the downfield shift of the non-equivalent 9-proton resonances on this residue (H9=4.21 and H9'=4.38 ppm) relative to the analogous pair in the non-acetylated FCHASE glycoside (H9=3.64 and H9'=3.88 ppm, from (Gilbert, M. et al., *J. Biol. Chem.*, 275, 3896-3906 (2000))). The esterification position was confirmed through the use of carbon-correlated proton spectra, where we observed a connectivity between the H9 protons, and the carbonyl functional group.

Figure 3A:
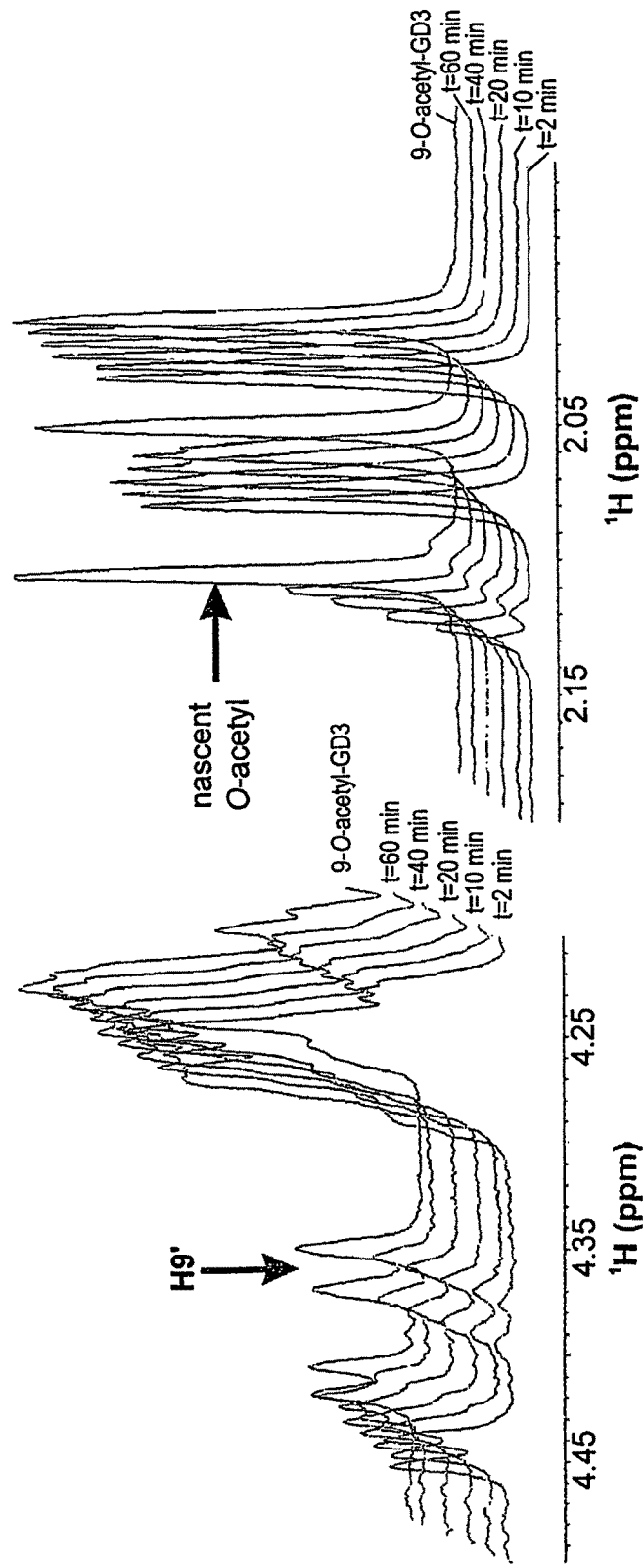
FIG. 3 demonstrates that MalE-Orf11$^{43446}$ transfers the O-acetyl group directly to C9 of NeuAc. (3A) Stacked $^1$H-NMR spectra of the acetylation of NeuAcα-2,-8-NeuAcα-2,3-Gal-β-1,4-Glc-FCHASE by the enzyme shows the buildup in signal of the H9' and O-acetyl resonances at various time-points following the initiation of the reaction. Signal from H9' is evident in the earliest spectra, indicating rapid formation of the 9-O-acetylated species. (3B) The signal intensity for the H9' (diamonds) and the O-acetyl (squares) resonances grow at almost identical rates, demonstrating direct transfer of the O-acetyl group to C9.
Figure 3B:
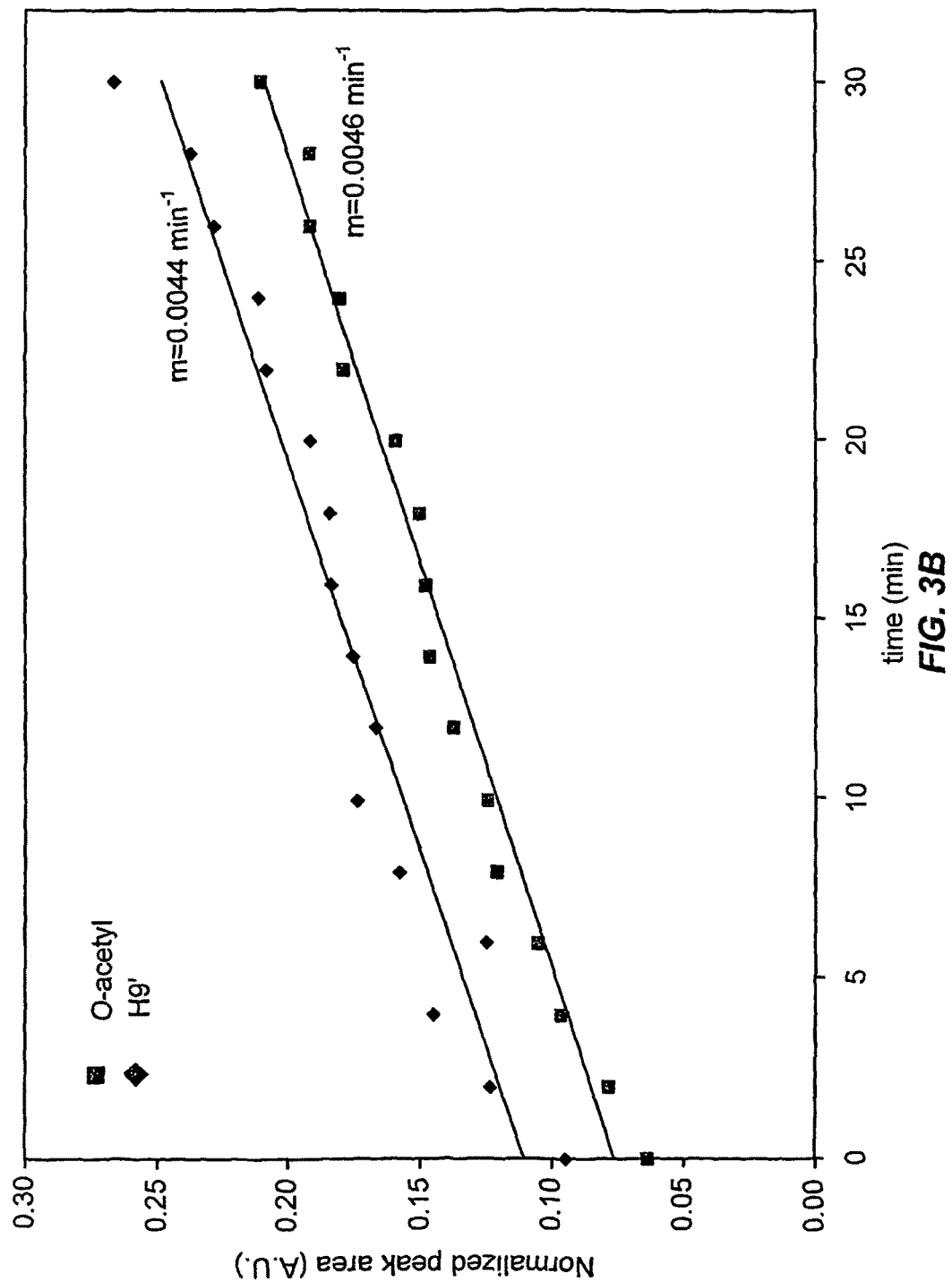

Our assignment of the O-acetyl group to the 9-position did not rule out the possibility that this isomer was formed post-enzymatically, as a result of migration from C7. In order to confirm the acceptor position on NeuAcα-2,8-NeuAcα-2,3-Gal-β-1,4-Glc-FCHASE, an O-acetylation reaction was followed in real-time. $^1$H spectra, acquired continuously at 2 minute intervals from the start of the reaction, demonstrate that MalE-Orf11$^{43446}$ transfers the O-acetyl group directly to C9. This is demonstrated by the growth of signal at 4.38 ppm in the earliest time-points following the addition of the enzyme (FIG. 3A). This resonance appears as a result of esterification at the 9-position, and flags the creation of the 9-O-acetylated species. In addition, the signal intensity of the nascent O-acetyl group grows at the same rate as H9' (FIG. 3B). This indicates that the formation of the O-acetyl ester bond, and the downfield shift of the H9-protons occurs in parallel, and argues strongly against the possibility of O-acetylation at C7, followed by migration.

Figure 6:
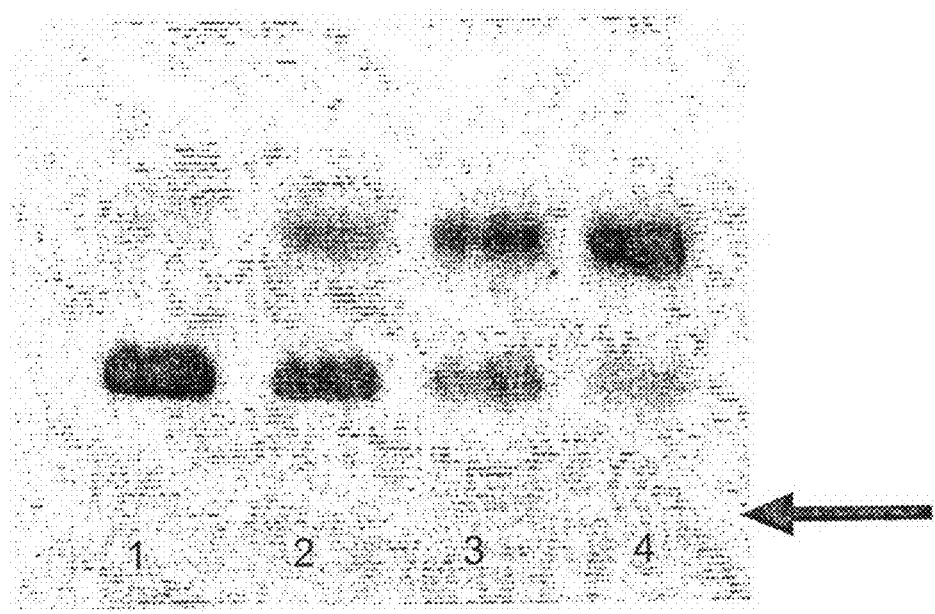
FIG. 6 demonstrates that the SOAT of *C. jejuni* strain ATCC 43438 can transfer propionyl groups in addition to acetyl groups to an acceptor molecule. Enhanced migration rate, indicating transfer of a propionyl group from propionyl-CoA to an acceptor, is observed when MalE-Orf11[43438] is incubated in the presence of propionyl-CoA and NeuAcα-2,-8-NeuAcα-2,3-Gal-β-1,4-Glc-FCHASE at 37° C. Lane 1: T=0, Lane 2: T=30 min, Lane 3: T=60 min. Lane 4: T=120 min. The arrow indicates the origin of migration. The image is shown with reversed gray scale levels.

Assay of Mal-Orf11$^{43438}$ with Alternate Donors:

Orf11 from *C. jejuni* ATCC 43438 was expressed as a MalE fusion construct (MalE-Orf11$^{43438}$) in *E. coli* and was purified by affinity chromatography. NeuAcα-2,8-NeuAcα-2,3-Gal-β-1,4-Glc-FCHASE at 0.5 mM was used as an acceptor. Propionyl-CoA was used as a donor at 2.5 mM. The conversion to 9-O-acetyl-NeuAcα-2,8-NeuAcα-2,3-Gal-β-1,4-Glc-FCHASE was complete (above 99%) after 15 min with acetyl-CoA as donor (data not shown). Propionyl-CoA was used as a donor, but at a lower rate than acetyl-CoA, since the conversion was about 80% after 120 min of incubation at 37° C. (FIG. 6)

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A reaction mixture comprising a recombinant sialate-O-acetyltransferase (SOAT) polypeptide having α-2,3 and α-2,8 activity, wherein the SOAT polypeptide comprises an amino acid sequence with at least 99% identity to SEQ ID NO:10 and wherein the SOAT polypeptide transfers an acetyl moiety from a donor substrate to an acceptor substrate.

2. The reaction mixture of claim 1, wherein the SOAT polypeptide comprises the amino acid sequence of SEQ ID NO:10.

3. A reaction mixture comprising a recombinant sialate-O-acetyltransferase (SOAT) polypeptide, wherein the SOAT polypeptide comprises an amino acid sequence with at least 99% identity to SEQ ID NO:10 and wherein the SOAT polypeptide transfers an acetyl moiety from a donor substrate to an acceptor substrate.

4. The reaction mixture of claim 3, wherein the SOAT polypeptide comprises the amino acid residues 78-216 of SEQ ID NO:10.

5. The reaction mixture of claim 3, wherein the SOAT polypeptide is encoded by a SOAT nucleic acid that is identical to a nucleic acid that is amplified from a *Campylobacter* genome using a first primer sequence comprising SEQ ID NO: 30 and a second primer sequence comprising SEQ ID NO: 31.

6. The reaction mixture of claim 3, wherein the SOAT polypeptide is an isolated SOAT polypeptide.

7. The reaction mixture of claim 3, comprising a recombinant host cell that expresses the SOAT polypeptide.

8. A recombinant sialate-O-acetyltransferase (SOAT) polypeptide, wherein the SOAT polypeptide comprises an amino acid sequence with at least 99% identity to SEQ ID NO:10 and wherein the SOAT polypeptide transfers an acetyl moiety from a donor substrate to an acceptor substrate.

9. The SOAT polypeptide of claim 8, wherein the SOAT polypeptide comprises the amino acid sequence of SEQ ID NO:10.

10. The SOAT polypeptide of claim 8, wherein the SOAT polypeptide comprises a purification tag.

* * * * *